US008883813B2

(12) United States Patent
Wustman

(10) Patent No.: US 8,883,813 B2
(45) Date of Patent: Nov. 11, 2014

(54) TREATMENT OF CNS DISORDERS ASSOCIATED WITH MUTATIONS IN GENES ENCODING LYSOSOMAL ENZYMES

(75) Inventor: Brandon Wustman, Princeton, NJ (US)

(73) Assignee: Amacus Therapeutics, Inc., Cranbury, NJ (US)

( * ) Notice: Subject to any disclaimer, the term of this patent is extended or adjusted under 35 U.S.C. 154(b) by 967 days.

(21) Appl. No.: 12/986,506

(22) Filed: Jan. 7, 2011

(65) Prior Publication Data

US 2011/0105560 A1 May 5, 2011

Related U.S. Application Data

(62) Division of application No. 11/449,528, filed on Jun. 8, 2006, now Pat. No. 7,964,617.

(60) Provisional application No. 60/689,120, filed on Jun. 8, 2005.

(51) Int. Cl.
*A01N 43/40* (2006.01)
*A61K 31/435* (2006.01)
*A01N 43/42* (2006.01)
*A61K 31/44* (2006.01)
*A01N 43/50* (2006.01)
*A61K 31/415* (2006.01)
*A01N 43/52* (2006.01)
*G01N 33/68* (2006.01)
*C12Q 1/68* (2006.01)

(52) U.S. Cl.
CPC ...... *C12Q 1/6876* (2013.01); *G01N 2800/2835* (2013.01); *G01N 33/6896* (2013.01); *C12Q 2600/156* (2013.01)
USPC ........... 514/277; 514/279; 514/299; 514/300; 514/396

(58) Field of Classification Search
CPC . A61K 31/41; A61K 31/4164; A61K 31/435; A61K 31/445
USPC .......... 514/277, 279, 299, 300, 385, 387, 396
See application file for complete search history.

(56) References Cited

U.S. PATENT DOCUMENTS

| | | | |
|---|---|---|---|
| 6,583,158 | B1 | 6/2003 | Fan et al. |
| 6,916,829 | B2 | 7/2005 | Fan et al. |
| 2002/0035072 | A1 | 3/2002 | Fan et al. |
| 2003/0119874 | A1 | 6/2003 | Fan et al. |
| 2007/0281975 | A1 | 12/2007 | Mugrage et al. |

FOREIGN PATENT DOCUMENTS

| | | |
|---|---|---|
| GB | 2 354 946 A | 4/2001 |
| WO | 2004 069190 A | 8/2004 |
| WO | 2005 046611 A | 5/2005 |
| WO | 2006 133446 A | 12/2006 |
| WO | 2008 144773 A | 11/2008 |

OTHER PUBLICATIONS

Selkoe, Nature Cell Biology, Nov. 2004, vol. 6, No. 11, pp. 1054-1061.
Webster's Ninth New Collegiate Dictionary, 2002, Definition of Prevention, p. 1.
Schlossmacher et al., New England Journal of Medicine, Feb. 2005, vol. 352, Issue 7, pp. 729-731.
Agid et al., Movement Disorders, 1999, vol. 14, No. 6, pp. 911-913.
Office Communication issued by the U.S.P.T.O. in U.S. Appl. No. 11/768,043 mailed Apr. 6, 2010; Interview Summary.
Office Communication issued by the U.S.P.T.O. in U.S. Appl. No. 11/768,043 mailed Jan. 5, 2010; Office Action.
Office Communication issued by the U.S.P.T.O. in U.S. Appl. No. 11/768,043 mailed Aug. 11, 2009; Office Action.
Sidransky, E., "Gaucher Disease "Complexity in a "Simple Disorder", Molecular Genetics and Metabolism, Academic Press, San Diego, CA, US, vol. 83, No. 1-2, Sep. 1, 2004, pp. 6-15.
Sidransky, E., "Gaucher Disease and parkinsonism", Molecular Genetics and Metabolism, Academic Press, San Diego CA, US, vol. 84, No. 4, Apr. 1, 2005, pp. 302-304.
Sawkar, A.R., et al., "Chemical Chaperones increase the cellular activity of N3705 beta-glucosidase: a therapeutic strategy for Gaucher disease", Proceedings of the National Academy of Sciences of USA, National Academy of Science, Washington DC, US, vol. 99, No. 24, Nov. 26, 2002, pp. 15428-15433.
Ruvinov et al., Monovalent Cations Partially Repair a Conformational Defect in a Mutant Tryptophan Synthase α2β2 Complex (β-E109A)*; J. Biol. Chem. 1995; 270; 17333-38.
Aharon-Peretz et al., "Mutations in the Glucocerebrosidase Gene and Parkinson's Disease in Ashkenazi Jews", New England Journal of Medicine, 2004; 351; 1972-77.
Clark et al., "Pilot Association Study of the β-Glucocerebrosidase N370S Allele and Parkinson's Disease in Subjects of Jewish Ethnicity", Movement Disorders, 2005; 20(1):100-103.
Tayebi et al., "Gaucher Disease with Parkinsonian Manifestations: Does Glucocerebrosidase Deficiency Contribute to a Vulnerability to Parkinsonism?" Mol. Genet. Metab. 2003; 79(2):104-9.
Wong et al., "Neuropathology Provides Clues to the Pathophysiology of Gaucher Disease", Molecular Genetics and Metabolism, 2004; 82:192-207.
Butters et al., "Therapeutic Applications of Imino Sugars in Lysosomal Storage Disorders", Current Topics in Medicinal Chemistry, 2003; 3:561-74.

*Primary Examiner* — Yong Chong
(74) *Attorney, Agent, or Firm* — Servilla Whitney LLC

(57) ABSTRACT

Described is a method for treating an individual having a neurological disorder with an associated mutation or mutations in a gene encoding a lysosomal enzyme. Specifically, the individual is administered a specific pharmacological chaperone for the lysosomal enzyme which increases trafficking of the protein from the ER to the lysosome in neural cells, with or without concomitantly increasing enzyme activity in neural cells. Restoration of trafficking relieves cell stress and other toxicities associated with accumulation of mutant proteins. Restoration of enzyme activity relieves substrate accumulation and pathologies associated with lipid accumulation. In a specific embodiment, the neurological disorder is Parkinson's disease or parkinsonism which is associated with mutations in glucocerebrosidase.

7 Claims, 13 Drawing Sheets

SEQ ID NO: 1 (GENBANK ACCESSION J03059)

```
   1 tctagaaaga cttcactgag atcatttaaa gaacaaaaag gatggctggg gtccagcgca
  61 gtggctcatg cctgtaatcc cagcactttc ggataccaag gcagcagatc acctgaggtc
 121 cagagtttca gaccagcctg gccaacatag tgaaacccca tctctactaa aaataaaaaa
 181 attagctgag catgttggag ggcacctgta atcccagcta cttgggaggc tgaggcagga
 241 gaatcactcg aacccaggag gtggaggttg cagtgagcca agatcacgcc actgcactcc
 301 agcctgggca acagagtgag actctgtctc aaaaaacaac aacaacaaaa aatacaaaca
 361 agagacaagt agttcccagg tgcctaccaa gtggtcaggc actgcactta cctcactgac
 421 tgcagtaacc acccttgag gttgtggcat tgcctccatt ttccaggcaa ggaaatgggc
 481 tgagagctgg gattagtcag gtcatgactg tgtgtgccac tcccgctaaa tctcatttga
 541 tgtggttcat gaggccacac catggacagc ttcctccttg tgtccactga ggatatggct
 601 ttgtacaaca ctttggtttt ttgaacgact ttacaaacct ccctgtcttg tgaggaagga
 661 agaacagtta ttaccatctg catctgatga tgaaacaagg gacgctgcag aggagccgca
 721 ctgaccactc cctccctcca gtcctgtcat cccactgcca gtgtcccacc ctcttgtgcc
 781 ctgcacttca ctggctaata accccccctca cttttcctc tgtgaagcca tcctggataa
 841 ttccccaccc acgaatggtc cctcctcatc tcagagagct ctccatgcac acctgttacc
 901 gtttctgtct ttatctgtaa atatctgtgt gtctgacttc catgcctcac acacctctat
 961 agggcaaaga ctgtcttaaa catcttggta gtgtcagtat tttgcacagt gaagttttt
1021 tttttaaatt atatcagctt tatttgtacc tttttgacat ttctatcaaa aaagaagtgt
1081 gcctgctgtg gttcccatcc tctgggattt aggagcctct accccattct ccatgcaaat
1141 ctgtgttcta ggctcttcct aaagttgtca cccatacatg ccctccagag ttttataggg
1201 catataatcg taacagatga gaggaagcca attgcccttt agaaatatgg ctgtgattgc
1261 ctcacttcct gtgtcatgtg acgctcctag tcatcacatg acccatccac atcgggaagc
1321 cggaattact tgcagggcta acctagtgcc tatagctaag gcaggtacct gcatccttgt
1381 ttttgtttag tggatcctct atccttcaga gactctggaa cccctgtggt cttctcttca
1441 tctaatgacc ctgaggggat ggagttttca agtccttcca gagaggtaag agagagagct
1501 cccaatcagc attgtcacag tgcttctgga atcctggcac tggaatttaa tgaatgacag
1561 actctctttg aatccagggc catcatggct ctttgagcaa ggcacagatg gagggagggg
1621 tcgaagttga aatgggtggg aagagtggtg gggagcatcc tgatttgggg tgggcagaga
1681 gttgtcatca gaagggttgc agggagagct gcacccaggt ttctgtgggc cttgtcctaa
1741 tgaatgtggg agaccgggcc atgggcaccc aaaggcagct aagccctgcc caggagagta
1801 gttgagggt ggagaggggc ttgcttttca gtcattcctc attctgtcct caggaatgtc
1861 ccaagccttt gagtagggta agcatcatgg ctggcagcct cacaggattg cttctacttc
1921 aggcagtgtc gtgggcatca ggtgagtgag tcaaggcagt ggggaggtag cacagagcct
1981 cccttctgcc tcatagtcct ttggtagcct tccagtaagc tggtggtaga cttttagtag
2041 gtgctcaata aatccttttg agtgactgag accaactttg gggtgaggat tttgttttt
```

FIGURE 4 (cont.)

```
2101 ttcttttgaa acagagtctt actctgttgc ctgggctgga gtgcagtggt gcaatttggg
2161 ctcattccaa cctctgcctc ccagattcaa gcgattctct tgcttcagct tcccaggtag
2221 ctgggattac aggcggccac cactacgccc agctaatttt tgtatttta gtagagacgg
2281 ggtttcacca tgctggcaag gcaggtctca aactcctcac ctcaggtgat ccgcccacct
2341 cggcctccta aagtgctagg attacaggtg tgagccctg cgccggcca agggtgagg
2401 aattttgaaa ccgtgttcag tctctcctag cagatgtgtc cattctccat gtcttcatca
2461 gacctcactc tgcttgtact ccctccctcc caggtgcccg ccctgcatc cctaaaagct
2521 tcggctacag ctcggtggtg tgtgtctgca atgccacata ctgtgactcc tttgaccccc
2581 cgacctttcc tgcccttggt accttcagcc gctatgagag tacacgcagt gggcgacgga
2641 tggagctgag tatggggccc atccaggcta atcacgggg cacaggtaac cattcaccc
2701 ctcacccct gggccaggct gggtcctcct agaggtaaat ggtgtcagtg atcaccatgg
2761 agtttcccgc tgggtactga tacccttatt ccctgtggat gtcctcaggc ctgctactga
2821 ccctgcagcc agaacagaag ttccagaaag tgaagggatt tggaggggcc atgacagatg
2881 ctgctgctct caacatcctt gccctgtcac cccctgccca aaatttgcta cttaaatcgt
2941 acttctctga agaaggtgag gaggaagggg acaagatgac atagagccat tgaaactttt
3001 cgttttttctt ttcttttttt aaaattttt tgaggcagaa tctcactctg cccattctgt
3061 cggcgagaca ggagtgcagt ggtgtgatct ccctcacag caacctctgc ctcccaggct
3121 atagtgattc tcctgcctca gcctcctgag tagctggaat tataggcgtg cgccactacc
3181 acctggctaa ttttgtatt tttagtagag acagggtttc atcatgttga ccaggctagt
3241 cttaaactcc tgacctcaaa tgatatacct gccttggcct cccgaagtgc tggaattaca
3301 agtgtgagcc accgagccca gcagacactt ttcttttttc tttttttt tttgagacag
3361 agtctcgcac tgtcacccag gctggagtgc agtggcacaa tctcagctca ctgcaacctc
3421 cacctcccgg gttcaggtga ttctcctgtc tcagcctctc gagtacctgg gattacaggt
3481 gcctgccacc acgcccggct aattttttgt attttagta gagacagggt ttcactatgt
3541 tggccaggat gattgcgaac tcctgacctc gtgatctgcc cacatcggcc tcccaaagtg
3601 ctgggattac atgcgtgagc cactgacact tttctttgcc ctttctttgg accctgactt
3661 ctgcccatcc ctgacatttg gttcctgttt taatgccctg tgaaataaga tttcgccgcc
3721 tatcatctgc taactgctac ggactcaggc tcagaaaggc ctgcgcttca cccaggtgcc
3781 agcctccaca ggttccaacc caggagccca gttcccttt ggccctgact cagacactat
3841 taggactggc aagtgataag cagagtccca tactctccta ttgactcgga ctaccatatc
3901 ttgatcatcc ttttctgtag gaatcggata taacatcatc cgggtaccca tggccagctg
3961 tgacttctcc atccgcacct acacctatgc agacacccct gatgatttcc agttgcacaa
4021 cttcagcctc ccagaggaag ataccaagct caaggtaggc attctagctt tttcaggccc
4081 tgagggccct gatgtctggg ggttgagaaa ctgtagggta ggtctgcttg tacagacatt
4141 ttgtccctg ctgttttgtc ctggggtgg gagggtggag ctaatggct gaaccggatg
4201 cactggttgg gctagtatgt gttccaactc tgggtgcttc tctcttcact acctttgtct
4261 ctagataccc ctgattcacc gagccctgca gttggcccag cgtcccgttt cactccttgc
4321 cagcccctgg acatcaccca cttggctcaa gaccaatgga gcggtgaatg ggaagggtc
```

FIGURE 4 (cont.)

```
4381 actcaaggga cagcccggag acatctacca ccagacctgg gccagatact ttgtgaagta
4441 agggatcagc aaggatgtgg gatcaggact ggcctcccat ttagccatgc tgatctgtgt
4501 cccaaccctc aacctagttc cacttccaga tctgcctgtc ctcagctcac ctttctacct
4561 tctgggcctt tcagccttgg gcctgtcaat cttgcccact ccatcaggct tcctgttctc
4621 tcggtctggc ccactttctt tttatttttc ttcttttttt ttttttgag aaggagtctc
4681 tctctctgtc acccaggctg gagtgctgtg gcgccatctt cactcactgt aacctctgcc
4741 tcctgagttc aagcaattct cctgcctcag ccttccaagt agctgggatt ataggcgcct
4801 gccaccaggc ccagctgatt tttctatttt tagtagagac ggggtttcgc caggctgttc
4861 tcgaactcct gaactcaagt gatccacctg cctcggcttc ccaaagtgct gggattacag
4921 gtgtgagcca ccacacccag ctggtctggt ccactttctt ggccggatca ttcatgacct
4981 ttctcttgcc aggttcctgg atgcctatgc tgagcacaag ttacagttct gggcagtgac
5041 agctgaaaat gagccttctg ctgggctgtt gagtggatac cccttccagt gcctgggctt
5101 caccccTgaa catcagcgag acttcattgc ccgtgaccta ggtcctaccc tcgccaacag
5161 tactcaccac aatgtccgcc tactcatgct ggatgaccaa cgcttgctgc tgccccactg
5221 ggcaaaggtg gtaaggcctg gacctccatg gtgctccagt gaccttcaaa tccagcatcc
5281 aaatgactgg ctcccaaact tagagcgatt tctctaccca actatggatt cctagagcac
5341 cattccctg gacctccagg gtgccatgga tcccacagtt gtcgcttgaa acctttctag
5401 gggctgggcg aggtggctca ctcatgcaaa cccagcactt tgggaagccg aggcgggtga
5461 tcacctgagg tcaggagttt aagaccaccc tggccaacgt gttgaaaccc tgtgtctact
5521 aaaatacaaa aaaaaaaaat tatctgggca tgatggtggg tgtctgtaat cccagctact
5581 caggaggctg agaagggaga atcagttgaa cccgggagat ggtggttgcg gtgagccgag
5641 atcgcgccac tgcactccag cctgggaggc tgagcgagac tccatctcga aacaaaacaa
5701 aacaaaacta tctaggctgg gggtggtggt tcatgtatgt atgtgtatat acatatatat
5761 gtgtttatat gtatatatat atacacacac acacatacat acacacacat acacacacaa
5821 attagctggg tgtggcaccc gtgtagtccc agctactcag gaggctaatg tgggaggatc
5881 agttgaccct aggaagtcaa ggctgcagtg agtcgtgatt gcgccactgt actccagccc
5941 gagtgacaga gtgacatcct gtctcaaaaa caaaaaaaaa tctccccaaa cctctctagt
6001 tgcattcttc ccgtcaccca actccaggat tcctacaaca ggaactagaa gttccagaag
6061 cctgtgtgca aggtccagga tcagttgctc ttcctttgca ggtactgaca gacccagaag
6121 cagctaaata tgttcatggc attgctgtac attggtacct ggactttctg gctccagcca
6181 aagccaccct aggggagaca caccgcctgt tccccaacac catgctcttt gcctcagagg
6241 cctgtgtggg ctccaagttc tgggagcaga gtgtgcggct aggctcctgg gatcgaggga
6301 tgcagtacag ccacagcatc atcacggtaa gccaccccag tctcccttcc tgcaaagcag
6361 acctcagacc tcttactagt ttcaccaaag actgacagaa gcccttcctg tccagctttc
6421 cccagctagc ctgccctttt gagcaactct ggggaaccat gattccctat cttcccttc
6481 cttcacaggt ctgcacacct cattgcccct tttgcaacta ctgaggcact tgcagctgcc
6541 tcagacttct cagctcccct tgagatgcct ggatcttcac accccaact ccttagctac
6601 taaggaatgt gcccctcaca gggctgacct acccacagct gcctctccca catgtgaccc
```

FIGURE 4 (cont.)

```
6661 ttacctacac tctctgggga cccccagtgt tgagcctttg tctctttgcc tttgtcctta
6721 ccctagaacc tcctgtacca tgtggtcggc tggaccgact ggaaccttgc cctgaacccc
6781 gaaggaggac ccaattgggt gcgtaacttt gtcgacagtc ccatcattgt agacatcacc
6841 aaggacacgt tttacaaaca gcccatgttc taccaccttg ccacttcag tgagtggag
6901 ggcgggcacc cccattccat accaggccta tcatctccta catcggatgg cttacatcac
6961 tctacaccac gagggagcag gaaggtgttc agggtggaac ctcggaagag gcacacccat
7021 cccctttgc accatggagg caggaagtga ctaggtagca acagaaaacc ccaatgcctg
7081 aggctggact gcgatgcaga aaagcagggt cagtgcccag cagcatggct ccaggcctag
7141 agagccaggg cagagcctct gcaggagtta tggggtgggt ccgtgggtgg gtgacttctt
7201 agatgagggt ttcatgggag gtaccccgag ggactctgac catctgttcc cacattcagc
7261 aagttcattc ctgagggctc ccagagagtg gggctggttg ccagtcagaa gaacgacctg
7321 gacgcagtgg cactgatgca tcccgatggc tctgctgttg tggtcgtgct aaaccggtga
7381 gggcaatggt gaggtctggg aagtgggctg aagacagcgt tgggggcctt ggcaggatca
7441 cactctcagc ttctcctccc tgctccctag ctcctctaag gatgtgcctc ttaccatcaa
7501 ggatcctgct gtgggcttcc tggagacaat ctcacctggc tactccattc acacctacct
7561 gtggcgtcgc cagtgatgga gcagatactc aaggaggcac tgggctcagc ctgggcatta
7621 aagggacaga gtcagctcac acgctgtctg tgactaaaga gggcacagca gggccagtgt
7681 gagcttacag cgacgtaagc ccaggggcaa tggtttgggt gactcacttt cccctctagg
7741 tggtgccagg ggctggaggc cctagaaaa agatcagtaa gccccagtgt ccccccagcc
7801 cccatgctta tgtgaacatg cgctgtgtgc tgcttgcttt ggaaactggg cctgggtcca
7861 ggcctagggt gagctcactg tccgtacaaa cacaagatca gggctgaggg taaggaaaag
7921 aagagactag gaaagctggg cccaaaactg gagactgttt gtctttcctg gagatgcaga
7981 actgggcccg tggagcagca gtgtcagcat cagggcggaa gccttaaagc agcagcgggt
8041 gtgcccaggc acccagatga ttcctatggc accagccagg aaaaatggca gctcttaaag
8101 gagaaaatgt ttgagcccag tcagtgtgag tggctttatt ctgggtggca gcaccccgtg
8161 tccggctgta ccaacaacga ggaggcacgg gggcctctgg aatgcatgag agtagaaaaa
8221 ccagtcttgg gagcgtgagg acaaatcatt cctcttcatc ctcctcagcc atgcccaggg
8281 tccgggtgcc tggggcccga gcaggcgttg cccgctggat ggagacaatg ccgctgagca
8341 aggcgtagcc caccatggct gccagtcctg ccagcacaga taggatctgg ttccggcgcc
8401 ggtatggctc ctcctcagtc tctgggcctg ctggtgtctg gcgttgcggt ggtacctcag
8461 ctgagggtca aggaaggaag gtgtgttagg agaactagtt cttggatccc tgcccactct
8521 ccccagggct gcccctccca tctgcccctt acctccatcc caggggaagt agagactgag
8581 aatgtgggta caataggcac agaggttgtg cagcccacgc aggtggacct gcagcttccc
8641 actgggcagc tttgcctgca gcagcagggc caagtagctg aagacgaagg cgtccaagga
8701 ggcagggctg gagcagagag agaagggtgg gatggaggag aaccactggg gtagaagggg
8761 taaagatgga gctggaggaa gagtcagcct tgggaggtgg gctctgggca gcaggcggcc
8821 accaggaagg acaggacaca cagttctaga
```

FIGURE 5

SEQ ID NO: 2 (GENBANK ACCESSION J03059)

MEFSSPSREECPKPLSRVSIMAGSLTGLLLLQAVSWASGARPCIPKSFGYSSVVCVCNATYCDSFDPPTFP
ALGTFSRYESTRSGRRMELSMGPIQANHTGTGLLLTLQPEQKFQKVKGFGGAMTDAAALNILALSPPAQNL
LLKSYFSEEGIGYNIIRVPMASCDFSIRTYTYADTPDDFQLHNFSLPEEDTKLKIPLIHRALQLAQRPVSL
LASPWTSPTWLKTNGAVNGKGSLKGQPGDIYHQTWARYFVKFLDAYAEHKLQFWAVTAENEPSAGLLSGYP
FQCLGFTPEHQRDFIARDLGPTLANSTHHNVRLLMLDDQRLLLPHWAKVVLTDPEAAKYVHGIAVHWYLDF
LAPAKATLGETHRLFPNTMLFASEACVGSKFWEQSVRLGSWDRGMQYSHSIITNLLYHVVGWTDWNLALNP
EGGPNWVRNFVDSPIIVDITKDTFYKQPMFYHLGHFSKFIPEGSQRVGLVASQKNDLDAVALMHPDGSAVV
VVLNRSSKDVPLTIKDPAVGFLETISPGYSIHTYLWRRQ

FIGURE 6

SEQ ID NO: 3 (GENBANK ACCESSION M16328)

```
   1 cattaggcc tatgaattat aagatacagt cactttaaaa tccactggaa ggctgaagag
  61 tgagttaaac ctcttataat gaatatacag tgaaaccagt agaggcattt tatttagggt
 121 tcctacaaga aagtgcttaa atagcatcga cgcctacatg ctacatcctg ttcagtctct
 181 gcctctgtga tgcagttggc cagcaaatat cctccaagtc atcatttgca tagtgctagg
 241 gataaaatga ggagcaatac caaatgctat acctgccctt atgggtctta tagtccaacg
 301 ggagaaaaag atattataca ataatcacg gaaataaat agaaaacgca tccttgtttt
 361 tgtttagtgg atcctctatc cttcagagac tctgaaccc ctgtggtctt ctcttcatct
 421 aatgaccctg aggggatgga gttttcaagt ccttccagag aggaatgtcc caagcctttg
 481 agtagggtaa gcatcatggc tggcagcctc acaggtttgc ttctacttca ggcagtgtcg
 541 tgggcatcag gtgcccgccc ctgcatccct aaaagcttcg gctacagctc ggtggtgtgt
 601 gtctgcaatg ccacatactg tgactccttt gacccccga cctttcctgc ccttggtacc
 661 ttcagccgct atgagagtac acgcagtggg cgacggatgg agctgagtat ggggcccatc
 721 caggctaatc acacgggcac aggcctgcta ctgaccctgc agccagaaca gaagttccag
 781 aaagtgaagg gatttggagg ggccatgaca gatgctgctg ctctcaacat ccttgccctg
 841 tcaccccctg cccaaaattt gctacttaaa tcgtacttct ctgaagaagg aatcggatat
 901 aacatcatcc gggtacccat ggccagctgt gacttctcca tccgcaccta cacctatgca
 961 gacacccctg atgatttcca gttgcacaac ttcagcctcc cagaggaaga taccaagctc
1021 aagatacccc tgattcaccg agccctgcag ttgcccagc gtcccgtttc actccttgcc
1081 agccctggga catcacccac ttggctcaag accaatggag cggtgaatgg gaaggggtca
1141 ctcaagggac agcccggaga catctaccac cagacctggg ccagatactt tgtgaagttc
1201 ctggatgcct atgctgagca caagttacag ttctgggcag tgacagctga aaatgagcct
1261 tctgctgggc tgttgagtgg atacccttc cagtgcctgg gcttcacccc tgaacatcag
1321 cgagacttca ttgcccgtga cctaggtcct accctcgcca acagtactca ccacaatgtc
1381 cgcctactca tgctggatga ccaacgcttg ctgctgcccc actgggcaaa ggtggtactg
1441 acagacccag aagcagctaa atatgttcat ggcattgctg tacattggta cctggacttt
1501 ctggctccag ccaaagccac cctaggggag acacaccgcc tgttccccaa caccatgctc
1561 tttgcctcag aggcctgtgt gggctccaag ttctgggagc agagtgtgcg gctaggctcc
1621 tgggatcgag ggatgcagta cagccacagc atcatcacga acctcctgta ccatgtggtc
1681 ggctggaccg actggaacct tgccctgaac cccgaaggag gacccaattg ggtgcgtaac
1741 tttgtcgaca gtccatcat tgtagacatc accaaggaca cgttttacaa acagcccatg
1801 ttctaccacc ttggccactt cagcaagttc attcctgagg gctcccagag agtggggctg
1861 gttgccagtc agaagaacga cctggacgca gtggcactga tgcatccga tggctctgct
1921 gttgtggtcg tgctaaaccg ctcctctaag gatgtgcctc ttaccatcaa ggatcctgct
1981 gtgggcttcc tggagacaat ctcacctggc tactccattc acacctacct gtggcatcgc
2041 cagtgatgga gcagatactc aaggaggcac tgggctcagc ctgggcatta aagggacaga
```

FIGURE 6 (cont.)

```
2101 gtcagctcac acgctgtctg tgactaaaga gggcacagca gggccagtgt gagcttacag
2161 cgacgtaagc caggggcaa tggtttgggt gactcacttt ccctctagg tggtgcccag
2221 ggctggaggc ccctagaaaa agatcagtaa gccccagtgt ccccccagcc cccatgctta
2281 tgtgaacatg cgctgtgtgc tgcttgcttt ggaaactngc ctgggtccag gcctagggtg
2341 agctcactgt ccgtacaaac acaagatcag ggctgagggt aaggaaaaga agagactagg
2401 aaagctgggc ccaaaactgg agactgtttg tctttcctag agatgcagaa ctgggcccgt
2461 ggagcagcag tgtcagcatc agggcggaag ccttaaagca gcagcgggtg tgcccaggca
2521 cccagatgat tcctatggca ccagccagga aaaatggcag ctcttaaagg agaaaatgtt
2581 tgagccc
```

FIGURE 7

SEQ ID NO: 4 (GENBANK ACCESSION M16328)

MAGSLTGLLLLQAVSWASGARPCIPKSFGYSSVVCVCNATYCDSFDPPTFPALGTFSRYESTRSGRRMELS
MGPIQANHTGTGLLLTLQPEQKFQKVKGFGGAMTDAAALNILALSPPAQNLLLKSYFSEEGIGYNIIRVPM
ASCDFSIRTYTYADTPDDFQLHNFSLPEEDTKLKIPLIHRALQLAQRPVSLLASPWTSPTWLKTNGAVNGK
GSLKGQPGDIYHQTWARYFVKFLDAYAEHKLQFWAVTAENEPSAGLLSGYPFQCLGFTPEHQRDFIARDLG
PTLANSTHHNVRLLMLDDQRLLLPHWAKVVLTDPEAAKYVHGIAVHWYLDFLAPAKATLGETHRLFPNTML
FASEACVGSKFWEQSVRLGSWDRGMQYSHSIITNLLYHVVGWTDWNLALNPEGGPNWVRNFVDSPIIVDIT
KDTFYKQPMFYHLGHFSKFIPEGSQRVGLVASQKNDLDAVALMHPDGSAVVVVLNRSSKDVPLTIKDPAVG
FLETISPGYSIHTYLWHRQ

TREATMENT OF CNS DISORDERS ASSOCIATED WITH MUTATIONS IN GENES ENCODING LYSOSOMAL ENZYMES

CROSS-REFERENCE TO RELATED APPLICATIONS

This application is a divisional application of U.S. patent application Ser. No. 11/449,528, filed on Jun. 8, 2006, issued as U.S. Pat. No. 7,964,617, which claims priority from U.S. Provisional Patent Application Serial No. 60/689,120, filed on Jun. 8, 2005, each of which is incorporated herein by reference in its entirety.

FIELD OF THE INVENTION

The present invention relates to a method for treating an individual having a neurological risk factor, condition, or disorder associated with a mutation or mutations in a lysosomal enzyme such as acid β-glucosidase. Specifically, the individual is administered a specific pharmacological chaperone for the lysosomal enzyme which increases trafficking of the protein from the ER to the lysosome in neural cells, and/or concomitantly increases enzyme activity in neural cells.

BACKGROUND OF THE INVENTION

Lysosomal storage disorders are a group of autosomal recessive diseases caused by the accumulation of cellular glycosphingolipids, glycogen, or mucopolysaccharides, due to defective hydrolytic enzymes. Examples of LSDs include but are not limited to Gaucher disease (Beutler et al., *The Metabolic and Molecular Bases of Inherited Disease*, 8th ed. 2001 Scriver et al., ed. pp. 3635-3668, McGraw-Hill, New York), $G_{M1}$-gangliosidosis (id. at pp 3775-3810), fucosidosis (*The Metabolic and Molecular Bases of Inherited Disease* 1995. Scriver, C. R., Beaudet, A. L., Sly, W. S, and Valle, D., ed pp. 2529-2561, McGraw-Hill, New York), mucopolysaccharidoses (id. at pp 3421-3452), Pompe disease (id. at pp. 3389-3420), Hurler-Scheie disease (Weismann et al., *Science*. 1970; 169, 72-74), Niemann-Pick A and B diseases, (*The Metabolic and Molecular Bases of Inherited Disease* 8th ed 2001. Scriver et al. ed., pp 3589-3610, McGraw-Hill, New York), and Fabry disease (id. at pp. 3733-3774). Others include Metachromatic Leukodystrophy, Kuf's Disease (Adult Neuronal Lipoid Lipofucsinosis) and Adrenoleukodystrophy. Each LSD is associated with a specific defective hydrolytic enzyme caused by one or more mutations which cause the enzyme to become conformationally unstable in the ER following synthesis, and thus, become targeted for degradation instead of trafficking through the Golgi to the native location in the lysosome.

Several LSDs have significant neurological involvement. For example, Gaucher disease is the most common LSD that is associated with the accumulation of glycosphingolipids (GSL) in cells, particularly monocytes and macrophages, of afflicted individuals. This aberrant build up of GSL results from a genetic deficiency (mutation) in the lysosomal enzyme acid β-glucosidase (Gba; glucocerebrosidase), the lysosomal hydrolase that breaks down the GSL glucosylceramide (GluCer). The disease has been classified into three clinical types, depending on neurological involvement and disease severity (Cox et al., *Q J Med*. 2001; 94: 399-402). Type 2 Gaucher disease is the rarest, most severe form, and is associated with early onset of acute neurologic disease. The characteristic feature of neuronopathic Gaucher disease is an abnormality of horizontal gaze. Afflicted patients develop progressive encephalopathy and extrapyrimidal symptoms such as rigidity and Parkinson's-like movement (parkinsonism). Most Type 2 Gaucher patients die in early childhood from apnea or aspiration due to neurological deterioration.

Type 3 Gaucher disease also has neurological involvement, although to a lesser extent than Type 2. Type 3 patients have central nervous system symptoms that include poor coordination of movements (ataxia), seizures, paralysis of the eye muscles, epilepsy, and dementia. A sub-classification of Type 3, Type 3c, is associated with hepatosplenomegaly, corneal opacities, progressive ataxia and dementia, and cardiac valve and aortic root calcification.

Other LSDs with neurological involvement include $G_{M1}$ gangliosidosis, which is associated with mutant β-galactosidase and results in neuronal lipidosis; $G_{M2}$ gangliosidosis (Tay-Sachs disease), which is associated with mutant hexosaminidase A and results in neuronal lipidosis; Niemann-Pick Disease, which is associated with mutant sphingomyelinase and also results in neuronal lipidosis; (Krabbe disease) galactocerebrosidase leukodystrophy; and neuronal ceroid lipofuscinoses, which is associated with mutant lysosomal proteases and results in neuronal lipidosis. Metachromatic Leukodystrophy is a deficiency of the enzyme arylsulfatase A and patients' symptoms include progressive movement disorders, seizures, cognitive disorders and also schizophrenia and psychiatric problems in addition to gastrointestinal disturbances. Kuf's Disease (Adult Neuronal Lipoid Lipofucsinosis) can manifest as psychiatric symptoms and seizures. Adrenal Leukodystrophy is a disorder which is characterized by progressive white-matter demyelination of the central nervous system and adrenocortical insufficiency.

Specific Pharmacological Chaperones

Recently, a specific pharmacological chaperone strategy has been developed to rescue unstable, mutated proteins from degradation presumably in the endoplasmic reticulum (ER) or in other cellular protein degradation/disposal systems. In particular embodiments, this paradigm shifting strategy employs small molecule reversible inhibitors which specifically bind to a defective lysosomal enzyme associated with a particular lysosomal disorder, stabilize the mutant enzyme in the ER, and "chaperone" the mutant enzyme so that it exits the ER. It was unexpectedly found that the inhibitors could bind with specificity to the enzyme during synthesis and folding in the ER, but could dissociate from the enzyme at its native location, thereby restoring its activity. In the absence of the chaperone, the mutated enzyme protein folds improperly in the ER (Ishii et al., *Biochem. Biophys. Res. Comm*. 1996; 220: 812-815), is retarded in its maturation to a final product, and is subsequently degraded in the ER. These specific chaperones are designated specific pharmacological chaperones (or active site-specific chaperones where the chaperone is a competitive inhibitor of an enzyme):

The term "active site-specific chaperone" evolved from initial studies using wild-type and mutant lysosomal enzymes. The catalytic portion of enzymes, i.e., the part where the enzyme binds to and interacts with its substrate, is generally known as the "active site in." The counterintuitive strategy of using a reversible competitive inhibitor of an enzyme (i.e., an enzyme inhibitor which competes with the substrate for binding to the catalytic center) to induce misfolded lysosomal enzymes to assume a stable molecular conformation, was first hypothesized by virtue of the ability of some competitive inhibitors to bind the catalytic centers during biosynthesis and stabilize enzymes. Thus, any stabilization that could be achieved in vivo in the ER during folding of a nascent enzyme, especially a mutant enzyme having a folding defect, would be beneficial since it would prevent binding of the endogenous ER "chaperones" that bind misfolded polypeptides and target them for degradation. Moreover, the competitive inhibitor was "reversible" as it dissociated from the enzyme once the enzyme reached the lysosome, where the inhibitor was out-competed by natural substrate.

The specific chaperone strategy has been described and exemplified for about 15 enzymes involved in LSDs in U.S. Pat. Nos. 6,274,597, 6,583,158, 6,589,964, and 6,599,919, to Fan et al., which are incorporated herein by reference in their entirety. For example, a small molecule derivative of galactose, 1-deoxygalactonojirimycin (DGJ), a potent competitive inhibitor of the mutant Fabry enzyme α-galactosidase A (α-Gal A), effectively increased in vitro stability of the human mutant α-Gal A (R301Q) at neutral pH, and it enhanced the mutant enzyme activity in lymphoblasts established from Fabry patients with R301Q or Q279E mutations. Furthermore, oral administration of DGJ to transgenic mice overexpressing a mutant (R301Q) α-Gal A substantially elevated the enzyme activity in major organs (Fan et al., *Nature Med.* 1999; 5: 112-115). Similar rescue of Gba from Gaucher patient cells has been described using another iminosugar, isofagomine (IFG), and its derivatives, described in U.S. Pat. No. 6,916,829 to Fan et al., and using other compounds specific for Gba (described in pending U.S. patent application Ser. Nos. 10/988,428, and 10/988,427, both filed Nov. 12, 2004).

LSD Enzyme Mutations and Neurological Disorders

Gba and Parkinson's. It has recently been discovered that there is a link between mutations in lysosomal enzymes and neurological disorders other than the LSDs. As one example, there is a well-established link between mutations in the Gba gene and Parkinson's disease. In one study, a group of 17 patients with rare, early onset, treatment-resistant parkinsonism were found to have at least one allele with a Gba missense mutation, including homozygous and heterozygous individuals for N370S, a mutation typically associated with type 1, non-neuronopathic disease (Tayebi et al., *Mol. Genet. Metab.* 2003; 79; 104-109). In another study, a population of 99 Ashkenazi Jews with idiopathic Parkinson's disease were evaluated for six Gba mutations (N370S, L444P, 84GG, V394L, and R496H). Thirty-one Parkinson's patients had one or two mutant Gba alleles: 23 were heterozygous for N370S; 3 were homozygous for N370S; 4 were heterozygous for 84GG; and 1 was heterozygous for R496H (Aharon-Peretz et al., *New Eng. J. Med.* 2004; 351: 1972-77). The frequency of a mutant N370S allele was 5 times that among 1573 normal subjects, and that of 84GG was 21 times that of normal subjects. Among patients with Parkinson's disease, patients carrying a Gba mutation also were younger than those who were not carriers. This study suggests that heterozygosity for a Gba mutation may predispose Ashkenazi Jews to Parkinson's disease.

Parkinson's and Gaucher diseases also share some pathological features, including neuronal loss, astrogliosis, and the presence of cytotoxic Lewy-body-like α-synuclein inclusions in hippocampal neurons (the CA2-4 region). A recent publication described the extent of neurological pathology in all three forms of Gaucher disease (Wong et al., *Mol. Genet. Metabol.* 2004; 38: 192-207). Abnormalities in cerebral cortical layers 3 and 5, hippocampal CA2-4, and layer 4b were found in Gaucher patients having all three types. Neuronal loss was evident only in patients with types 2 and 3, whereas type 1 patients presented with astrogliosis (Wong et al., supra). Two patients with type 1 Gaucher and parkinsonism/dementia exhibited α-synuclein positive inclusions in hippocampal CA2-4 neurons, one patient had brainstem-type and cortical-type Lewy bodies, and one had marked neuronal loss of substantia nigra neurons (Wong et al., supra). In summary, all 4 patients with parkinsonism and dementia had hippocampal CA2-4 gliosis, and neuronal depletion, gliosis, and brainstem-type Lewy bodies in the substantia nigra.

Several mouse models also demonstrate this link between Gba and Parkinson's. The optimal in vitro hydrolase activity of Gba requires saposin C, an activator protein that derives from a precursor, prosaposin. Transgenic mice expressing low levels (4-45% of wild type) of prosaposin and saposins (PS-NA), backcrossed into mice with specific point mutations (V394LN394L or D409H/D409H) of Gba, has several CNS phenotypes similar to PD phenotypes including: gait ataxia, tremor, shaking to the point of falling over, and a neurogenic bladder (Sun et al., *J Lipid Res.* 2005. 46(10): 2102-13).

The specific pharmacological chaperone work described above established the ability to restore enough function to a mutant enzyme (conformational mutation) to reduce or even eliminate the build-up of toxic quantities of lipid substrate in the LSDs. However, it was not clear that this approach could affect heterozygous individuals, or individuals with homozygous mutations who are not diagnosed with an LSD according to current criteria, but are at risk of developing a neurological condition or disorder due to the effects of the mutation, or individuals who are diagnosed with having lysosomal storage disorders but have mutations in addition to or other than conformational mutations which render the protein non-functional. All of these populations are at risk of developing a neurological disorder due to either toxic gain of function, pathologic loss of function, or a combination. Thus, there remains a need in the art to be able to identify causative factors and address the consequences of such mutations in these patient populations.

SUMMARY OF THE INVENTION

The present invention provides a method for the treatment of a neurological disorder in an individual, wherein the neurological disorder is associated with a mutation in the gene encoding a lysosomal enzyme, by administering an effective amount of a specific pharmacological chaperone to treat the neurological disorder.

In one embodiment, the individual is homozygous for the mutation. In another embodiment, the individual is hemizygous, heterozygous or compound heterozygous for the mutation.

In one embodiment, the mutation results in the enzyme being a conformational mutant.

In a specific embodiment, wherein the chaperone increases trafficking of the mutant enzyme from the endoplasmic reticulum and may or may not concomitantly restore enzyme activity.

In another embodiment, the mutation results in increased amounts of, or aggregation, of another cellular substance, such as a lipid or another protein or protein fragment, such as α-synuclein.

In a specific embodiment of the present invention, the lysosomal enzyme is glucocerebrosidase and the neurological disorder is Parkinson's disease or parkinsonism.

In another specific embodiment, the Parkinson's disease is early-onset Parkinson's disease.

In some embodiments of the invention, the specific pharmacological chaperone is an inhibitor of the lysosomal enzyme, and the inhibitor is a reversible or competitive inhibitor or both.

In a specific embodiment, the pharmacological chaperone for glucocerebrosidase is isofagomine or (5R,6R,7S,8S)-5-hydroxymethyl-2-octyl-5,6,7,8-tetrahydroimidazo[1,2-a]pyridine-6,7,8-triol.

The present invention also provides a method for diagnosing a neurological disorder associated with a mutant lysosomal enzyme, by screening an individual who exhibits neurological symptoms for a mutation in one or more lysosomal enzymes.

In one embodiment, the mutation results in an enzyme that is a conformational mutant.

In another embodiment, the screening is done by determining decreased enzyme activity from a biological sample from the individual compared with a biological sample from a healthy individual.

In a specific embodiment, the neurological disorder diagnosed is parkinsonism or Parkinson's disease.

BRIEF DESCRIPTION OF THE DRAWINGS

FIG. 1 demonstrates the levels of Gba activity in the brains from L444P transgenic mice treated with the specific pharmacological chaperone isofagomine (1A). Also depicted is the Gba activity level in the brain following a washout and re-treatment period (1B).

FIGS. 2A-N. FIG. 2E-F shows an overlay of dual Gba and LAMP-1 staining in Gaucher fibroblasts. Also depicted is a dual overlay (LAMP-1 and Gba) of Gaucher cells treated with the specific pharmacological chaperone isofagomine (2G-H) and the specific pharmacological chaperone C-benzyl-isofagomine (2I-J). Lastly, FIGS. 2K-N show staining of Gaucher cells for Gba only. Control Gaucher cells were stained with secondary antibody only (2K), or were not treated (2L), or were treated with isofagomine (2M) or C-benzyl-isofagomine (2N).

FIGS. 3A-I.

FIG. 4. FIG. 4 depicts the gene encoding human acid β-glucosidase, also referred to as glucocerebrosidase or Gba (GenBank Accession No. J03059; SEQ ID NO: 1).

FIG. 5. FIG. 5 depicts the wild-type human Gba protein. The Gba protein consists of 536 amino acids and is in GenBank Accession No. J03059 (SEQ ID NO: 2).

FIG. 6. FIG. 6 depicts the homologous pseudogene for Gba located about 16 kb downstream of the Gba gene (GenBank Accession No. M16328; SEQ ID NO: 3).

FIG. 7. FIG. 7 depicts the polypeptide encoded by the homologous pseudogene for Gba (SEQ ID NO: 4).

DETAILED DESCRIPTION

Figure 1:
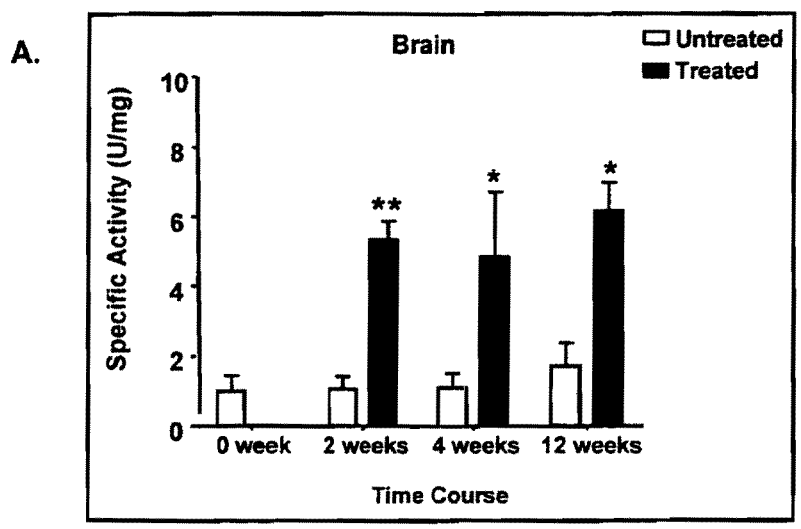
FIG. 1.
Figure 1:
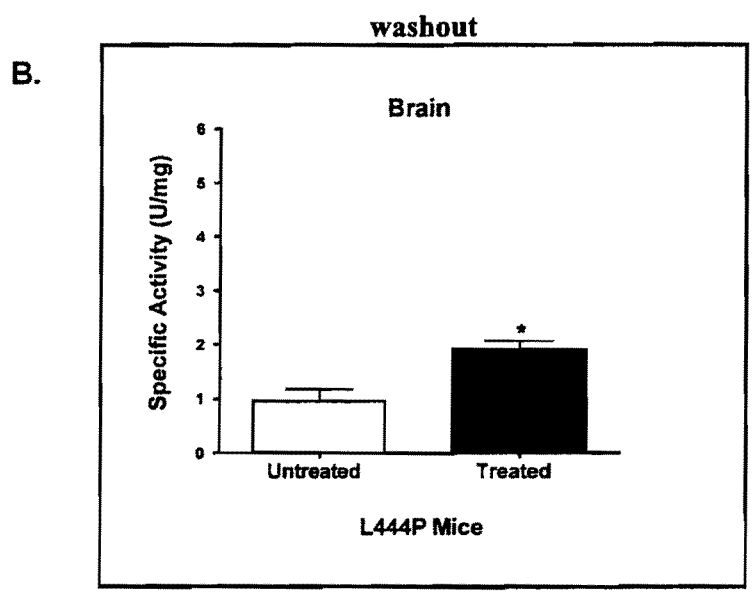

The present invention is based on the discovery that neurological disorders presenting in individuals not diagnosed with lysosomal storage disorders may be linked to mutations in lysosomal enzymes. Accordingly, the present invention, a specific pharmacologic chaperone, such as an ASSC, can ameliorate both gain of function and loss of function pathologies associated with mutations of lysosomal enzymes which are linked with neurological risk factors, conditions, or disorders. The chaperones can induce proper trafficking of mutant proteins at a sufficient level to inhibit, even to the point of prevention, toxic accumulation associated with the build up of misfolded, mutant proteins (i.e., gain of function), which in turn can effect neurological function. In some cases where the mutation only impairs folding and trafficking of the protein to its native cellular location and is not, e.g., a mutant which impairs catalytic or other activity of the protein, or is a nonsense mutant, the chaperones also can restore activity to the mutant protein, thereby addressing pathologies associated with the protein's loss of function, such as substrate accumulation or even aggregation of other toxic proteins or fragments which results from accumulation of substrate.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "Gaucher disease" includes Type 1, Type 2 and Type 3, and intermediates and subgroups thereof based on phenotypic manifestations.

A "neurological disorder" refers to any central nervous system (CNS) or peripheral nervous system (PNS) disease that is associated with neuronal or glial cell defects including but not limited to neuronal loss, neuronal degeneration, neuronal demyelination, gliosis (i.e., astrogliosis), or neuronal or extraneuronal accumulation of aberrant proteins or toxins (e.g., β-amyloid, or α-synuclein). The neurological disorder can be chronic or acute. Exemplary neurological disorders include but are not limited to Gaucher disease and other LSDs including Fabry disease, Tay-Sachs disease, Pompe disease, and the mucopolysaccharidoses; Parkinson's disease; Alzheimer's disease; Amyotrophic Lateral Sclerosis (ALS); Multiple Sclerosis (MS); Huntington's disease; Fredrich's ataxia; Mild Cognitive Impairment; and movement disorders (including ataxia, cerebral palsy, choreoathetosis, dystonia, Tourette's syndrome, kernicterus); tremor disorders, leukodystrophies (including adrenoleukodystrophy, metachromatic leukodystrophy, Canavan disease, Alexander disease, Pelizaeus-Merzbacher disease); neuronal ceroid lipofucsinoses; ataxia telangectasia; and Rett Syndrome. This term also includes cerebrovascular events such as stroke and ischemic attacks.

As used herein, the term "neurological disorder" also includes persons at risk of developing a neurological disorder, disease or condition as well as persons already diagnosed with a neurological disorder, disease or condition.

A "neurological disorder associated with a mutation in a lysosomal enzyme" refers to any neurological disorder in which a mutation or mutations in the gene encoding the enzyme are also present when assessed in individuals having the neurological disorder, compared with individuals not having or at risk of developing the neurological disorder (i.e., healthy individuals). In specific embodiments, the neurological disorder associated with Gba (Gaucher) mutations is Parkinson's disease or parkinsonism.

The term "human Gba gene" refers to the gene encoding acid β-glucosidase, also referred to as glucocerebrosidase or Gba. The Gba gene is on chromosome 1q21 and involves 11 exons (GenBank Accession No. J03059; SEQ ID NO: 1).

There is also a homologous pseudogene for Gba located about 16 kb downstream of the Gba gene (GenBank Accession No. M16328; SEQ ID NO: 3).

The "human Gba" protein refers to the wild-type human Gba protein. The Gba protein consists of 536 amino acids and is in GenBank Accession No. J03059 (SEQ ID NO: 2). The polypeptide encoded by the above-referenced pseudogene is depicted in SEQ ID NO: 4.

As used herein, the term "pharmacological chaperone," or sometimes "specific pharmacological chaperone" ("SPC"), refers to a molecule that specifically binds to a protein such as a lysosomal enzyme (e.g., Gba) and has one or more of the following effects: (i) enhancing the formation of a stable molecular conformation of the protein; (ii) inducing trafficking of the protein from the ER to another cellular location, preferably a native cellular location, i.e., preventing ER-associated degradation of the protein; (iii) preventing aggregation of misfolded proteins; (iv) restoring or enhancing at least partial wild-type function, stability, and/or activity to the protein; and/or improving the phenotype or function of the cell harboring the protein. Thus, a pharmacological chaperone for a protein is a molecule that binds to the protein resulting in proper folding, trafficking, non-aggregation, and activity of the protein. As used herein, this term does not refer to endogenous chaperones, such as BiP, or to non-specific agents which have demonstrated non-specific chaperone activity against various proteins, such as glycerol, DMSO or deuterated water, sometimes called "chemical chaperones" (see Sato et al., *Biochem Biophys Acta*. 1988; 126(2): 756-62; Welch et al., *Cell Stress and Chaperones* 1996; 1(2):109-115; Welch et al., *Journal of Bioenergetics and Biomembranes* 1997; 29(5):491-502; U.S. Pat. Nos. 5,900,360; 6,270,954; and 6,541,195).

As used herein, the term "specifically binds" refers to the interaction of a pharmacological chaperone with a specific protein, specifically, an interaction with amino acid residues of a protein that directly participate in contacting the pharmacological chaperone. A compound that specifically binds to a target protein, e.g., Gba, means that it binds to and exerts a pharmacological chaperone effect on Gba and not a generic group of related or unrelated proteins. The amino acid residues of the protein that interact with any given pharmacological chaperone may or may not be within the protein's "active site." Specific binding can be evaluated through routine binding assays or through structural studies, e.g., co-crystallization, NMR, and the like.

The term "wild-type protein" refers to the nucleotide sequences encoding functional proteins, and polypeptide sequences encoded by the aforementioned nucleotide sequences, and any other nucleotide sequences that encode a functional polypeptide (having the same functional properties and binding affinities as the aforementioned polypeptide sequences), such as allelic variants in normal individuals, that have the ability to achieve a functional conformation in the ER, achieve proper localization within the cell, and exhibit wild-type activity (e.g., GluCer hydrolysis).

As used herein the term "mutant protein" refers to a polypeptide translated from a gene containing a genetic mutation that results in an altered amino acid sequence. In one embodiment, the mutation results in a protein that does not achieve a native conformation under the conditions normally present in the ER, when compared with wild-type protein, or exhibits decreased stability or activity as compared with wild-type protein. This type of mutation is referred to herein as a "conformational mutation," and the protein bearing such a mutation is referred as a "conformational mutant." The failure to achieve this conformation results in the protein being degraded or aggregated, rather than being transported through a normal pathway in the protein transport system to its native location in the cell or into the extracellular environment.

In another embodiment, the protein has another mutation in addition to or other than a conformational mutant, which permits translation, and hence ER accumulation of all or portion of the protein (which protein may or may not retain wild-type activity).

In some embodiments, a mutation may occur in a non-coding part of the gene encoding the protein that results in less efficient expression of the protein, e.g., a mutation that affects transcription efficiency, splicing efficiency, mRNA stability, and the like. By enhancing the level of expression of wild-type as well as conformational mutant variants of the protein, administration of a pharmacological chaperone can ameliorate a deficit resulting from such inefficient protein expression.

Other mutations can result in decreased enzymatic activity or a more rapid turnover.

Specific embodiments of Gba mutants associated with neuronopathic diseases include but are not limited to: N370S, L444P, K198T, D409H, R496H, V394L, 84GG, and R329c.

A heterozygous mutation of Gba refers to a genotype in which there is one wild-type allele and one mutant allele, e.g., N370S/wt. A heterozygous Gba mutation also refers to a genotype in which there are two mutated alleles, each with a different mutation, e.g., N370S/L444P. This term also includes the mutant/null genotype, i.e., N370S/null. This definition is also applicable when referring to heterozygous mutations in other lysosomal enzymes.

A homozygous Gba mutation refers to a genotype in which there are two mutant Gba alleles in which the mutations are same, e.g., N370S/N370S. This definition is also applicable when referring to homozygous mutations in other lysosomal enzymes.

The term "stabilize a proper conformation" refers to the ability of a pharmacological chaperone to induce or stabilize a conformation of a mutated protein that is functionally identical to the conformation of the wild-type counterpart. The term "functionally identical" means that while there may be minor variations in the conformation (almost all proteins exhibit some conformational flexibility in their physiological state), conformational flexibility does not result in (1) protein aggregation, (2) elimination through the endoplasmic reticulum-associated degradation pathway, (3) impairment of protein function, e.g., Gba activity, and/or (4) improper transport within the cell, e.g., localization to the lysosome, to a greater or lesser degree than that of the wild-type protein.

The term "stable molecular conformation" refers to a conformation of a protein, i.e., Gba, induced by a specific pharmacological chaperone, that provides at least partial wild-type function in the cell. For example, a stable molecular conformation of a mutant protein would be one where the protein escapes from the ER and trafficks to the native cellular location as does a wild-type Gba (e.g., the lysosome), instead of misfolding and being degraded. In addition, a stable molecular conformation of a mutated protein may also possess full or partial activity, e.g., GluCer hydrolysis. However, it is not necessary that the stable molecular conformation have all of the functional attributes of the wild-type protein.

The term "wild-type activity" refers to the normal physiological function of a protein, e.g., Gba, in a cell. For example, Gba activity includes folding and trafficking from the ER to the lysosome, with or without the concomitant ability to hydrolyze a substrate such as GluCer or 4-methylumbelliferyl (4-MU). Such functionality can be tested by any means known to establish functionality of such a protein.

Certain tests may evaluate attributes of a protein that may or may not correspond to its actual in vivo function, but nevertheless are aggregate surrogates of protein functionality, and wild-type behavior in such tests is an acceptable consequence of the protein folding rescue or enhancement techniques of the invention. One such activity in accordance with the invention is appropriate transport of a mutant protein, e.g., Gba from the endoplasmic reticulum to the native cellular location e.g., lysosome, or into the extracelluar environment.

The term "endogenous expression" refers to the normal physiological expression of a protein in cells in an individual not having or suspected of having a CNS disease or disorder associated with a deficiency, overexpression, or other defect, of a protein such as in the nucleic acid or polypeptide sequence which inhibit its expression, activity, or stability. This term also refers to the expression of the protein in cell types in which it is normal for the protein to be expressed and does not include expression in cells or cell types, e.g., tumors, in which the protein is not expressed in healthy individuals.

As used herein, the terms "enhance expression" or "increase expression" refer to increasing the amount of a polypeptide that adopts a functional conformation in a cell contacted with a pharmacological chaperone specific for that protein, relative to its expression in a cell (preferably of the same cell-type or the same cell, e.g., at an earlier time) not contacted with the pharmacological chaperone specific for that protein. The aforementioned terms alternatively mean increasing the efficiency of transport of a polypeptide from the ER in a cell contacted with a pharmacological chaperone specific for that protein, relative to the efficiency of transport of a wild-type counterpart in a cell (preferably of the same cell, e.g., at an earlier time, or the same cell type) not contacted with the pharmacological chaperone specific for that protein.

As used herein, the term "efficiency of transport" refers to the ability of a mutant protein to be transported out of the endoplasmic reticulum to its native location within the cell, to another location within the cell, to the cell membrane, or into the extracellular environment.

A "competitive inhibitor" of an enzyme can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

Non-classical competitive inhibition occurs when the inhibitor binds remotely to the active site, creating a conformational change in the enzyme such that the substrate can no longer bind to it. In non-classical competitive inhibition, the binding of substrate at the active site prevents the binding of inhibitor at a separate site and vice versa. This includes allosteric inhibition.

A "linear mixed-type inhibitor" of an enzyme is a type of competitive inhibitor that allows the substrate to bind, but reduces its affinity, so the Km is increased and the Vmax is decreased.

A "non-competitive inhibitor" refers to a compound that forms strong bonds with an enzyme and may not be displaced by the addition of excess substrate, i.e., non-competitive inhibitors may be irreversible. A non-competitive inhibitor may bind at, near, or remote from the active site of an enzyme or protein, and in connection with enzymes, has no effect on the Km but decreases the Vmax. Uncompetitive inhibition refers to a situation in which inhibitor binds only to the enzyme-substrate (ES) complex. The enzyme becomes inactive when inhibitor binds. This differs from non-classical competitive inhibitors which can bind to the enzyme in the absence of substrate.

The term "Vmax" refers to the maximum initial velocity of an enzyme catalyzed reaction, i.e., at saturating substrate levels. The term "Km" is the substrate concentration required to achieve ½ Vmax.

A "responder" is an individual diagnosed with a neurological disorder associated with a lysosomal enzyme mutation and treated according to the presently claimed method who exhibits an improvement in, amelioration, or prevention of, one or more clinical symptoms, or improvement or reversal of one or more surrogate clinical markers. As one example, a "responder" for individuals with Parkinson's disease (having concomitant Gba mutations) is one who exhibits improvement in, amelioration, or prevention of, one or more clinical symptoms, or improvement or reversal of one or more surrogate clinical markers including but not limited to: neuronal loss, astrogliosis, and the presence of intraneuronal Lewy-body-like α-synuclein inclusions in CA2-3 neurons.

The terms "therapeutically effective dose" and "effective amount" refer to the amount of the specific pharmacological chaperone that is sufficient to result in a therapeutic response. A therapeutic response may be any response that a user (e.g., a clinician) will recognize as an effective response to the therapy, such as by assessing symptoms and surrogate clinical markers. Thus, a therapeutic response will generally be an amelioration of one or more symptoms of a disease or disorder, e.g., a neurological disorder.

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Molecular Biology Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); Oligonucleotide Synthesis (M. J. Gait ed. 1984); *Nucleic Acid Hybridization* [B. D. Hames & S. J. Higgins eds. (1985)]; Transcription And Translation [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material, such as a Gba nucleic acid or polypeptide, that has been isolated under conditions that reduce or eliminate unrelated materials, i.e., contaminants. For example, a purified protein is preferably substantially free of other proteins or nucleic acids with which it is associated in a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. According to the present invention, the host cell is modified to express a mutant or wild-type lysosomal enzyme nucleic acid and polypeptide. Host cells can further be used for screening or other assays. A "recombinant DNA molecule" is a DNA molecule that has undergone a molecular biological manipulation. Exemplary host cells for use in the present invention are HEK293 cells, COS cells, and CHO cells.

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "coding sequence" or a sequence "encoding" an expression product, such as a RNA or polypeptide, is a nucleotide sequence that, when expressed, results in the production of that RNA or polypeptide, e.g., the Gba nucleotide sequence encodes an amino acid sequence for a Gba polypeptide (protein). A coding sequence for the protein may include a start codon (usually ATG) and a stop codon.

The term "gene", also called a "structural gene" means a DNA sequence that codes for or corresponds to a particular sequence of amino acids which comprise all or part of one or more lysosomal proteins, and may or may not include regulatory DNA sequences, such as promoter sequences, which determine for example the conditions under which the gene is expressed.

The terms "express" and "expression", when used in the context of producing an amino acid sequence from a nucleic acid sequence, means allowing or causing the information in a gene or DNA sequence to become manifest, for example producing a Gba protein by activating the cellular functions involved in transcription and translation of the corresponding Gba gene or DNA sequence. A DNA sequence is expressed in or by a cell to form an "expression product" such as a Gba protein. The expression product itself, e.g., the resulting protein, may also be said to be "expressed" by the cell. An expression product can be characterized as intracellular, extracellular or secreted. According to the present invention, the protein is expressed intracelluarly in neurons.

The term "intracellular" means something that is inside a cell. The term "extracellular" means something that is outside a cell. A substance is "secreted" by a cell if it appears in significant measure outside the cell, from somewhere on or inside the cell.

The term "heterologous" refers to a combination of elements not naturally occurring in combination. For example, heterologous DNA refers to DNA not naturally located in the cell, or in a chromosomal site of the cell. Preferably, the heterologous DNA includes a gene foreign to the cell. A heterologous expression regulatory element is an element operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed, e.g., an *E. coli* cell.

The term "transformation" refers to the process by which DNA, i.e., a nucleic acid encoding a lysosomal enzyme polypeptide, is introduced from the surrounding medium into a host cell.

The term "transduction" refers to the introduction of DNA, i.e., a nucleic acid encoding a Gba polypeptide, into a prokaryotic host cell, e.g., into a prokaryotic host cell via a bacterial virus, or bacteriophage. A prokaryotic or eukaryotic host cell that receives and expresses introduced DNA or RNA has been "transformed" or "transduced" and is a "transformant" or a "clone." The DNA or RNA introduced into a host cell can come from any source, including cells of the same genus or species as the host cell, or cells of a different genus or species, or synthetic sequences.

The term "recombinantly engineered cell" refers to any prokaryotic or eukaryotic cell that has been manipulated to express or overexpress the nucleic acid of interest, i.e., a nucleic acid encoding a Gba polypeptide, by any appropriate method, including transfection, transformation or transduction. This term also includes endogenous activation of a nucleic acid in a cell that does not normally express that gene product or that expresses the gene product at a sub-optimal level.

The term "transfection" means the introduction of a foreign" (i.e., extrinsic or extracellular) nucleic acid into a cell. The "foreign" nucleic acid includes a gene, DNA or RNA sequence to a host cell, so that the host cell will replicate the DNA and express the introduced gene or sequence to produce a desired substance, typically a protein or enzyme coded by the introduced gene or sequence. The introduced gene, i.e., a nucleic acid encoding a Gba polypeptide, or sequence may also be called a "cloned" gene or sequence, may include regulatory or control sequences, such as start, stop, promoter, signal, secretion, or other sequences used by a cell's genetic machinery. The gene or sequence may include nonfunctional sequences or sequences with no known function. DNA may be introduced either as an extrachromosomal element or by chromosomal integration or a host cell that receives and expresses introduced DNA or RNA.

Depending on the host cell used, transformation/transfection is done using standard techniques appropriate to such cells. The calcium treatment employing calcium chloride, as described in section 1.82 of Sambrook et al., 1989 supra, is generally used for bacterial cells that contain substantial cell-wall barriers. Another method for transformation employs polyethylene glycol/DMSO, as described in Chung and Miller (*Nucleic Acids Res.* 1988, 16:3580). Yet another method is the use of the technique termed electroporation. Alternatively, where a viral vector is used, the host cells can be infected by the virus containing the gene of interest.

The terms "vector", "cloning vector" and "expression vector" mean the vehicle by which a DNA or RNA sequence (e.g., a Gba gene) can be introduced into a host cell, so as to transform the host and promote expression (e.g., transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms.

A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), pCXN and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

A wide variety of host/expression vector combinations (i.e., expression systems) may be employed in expressing the proteins of interest. Useful expression vectors, for example, may consist of segments of chromosomal, non-chromosomal and synthetic DNA sequences. Suitable vectors include known bacterial plasmids, e.g., *E. coli* plasmids col E1, pCR1, pBR322, pMal-C2, pET, pGEX (Smith et al., Gene 67:31-40, 1988), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors derived from combinations of plasmids and phage DNAs, such as plasmids that have been modified to employ phage DNA or other expression control sequences; and the like. Another common expression system uses insect host cells and baculovirus vectors.

Exemplary expression vectors commercially available for use in mammalian cells include pMEP4, pCEP4, pLXSN, PXT1, pcDNA3 series, pcDNA4 series, pCMV-Script, pCMV-Tag and other CMV-based vectors, pVP22, pVAX1, pUB6. For transfection of mammalian cells, viral vectors include adeno-associated viral vectors, pox viruses, and retroviruses. Mammalian expression vectors are routine and well known in the art.

The host cells can inherently also harbor the polypeptide of interest, e.g., Gba. For heterologous polypeptides such as Gba, the heterologous nucleic acid (e.g., cDNA) is suitably inserted into a replicable vector for expression in the culture medium under the control of a suitable promoter. As noted above, many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes, and a promoter.

The DNA encoding the Gba polypeptide may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, 1 pp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline; (b) complement auxotrophic deficiencies; or (c) supply critical nutrients not available from complex media. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide also contains an inducible promoter that is recognized by the host organism and is operably linked to the nucleic acid encoding the polypeptide of interest.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase.

A coding sequence is "under the control" of or "operatively associated with" transcriptional and translational control sequences in a cell when RNA polymerase transcribes the coding sequence into mRNA, which is then trans-RNA spliced (if it contains introns) and translated into the protein encoded by the coding sequence.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform bacterial strains, and successful transformants are selected by ampicillin or tetracycline resistance where appropriate. Plasmids from the transformants are prepared, analyzed by restriction endonuclease digestion, and/or sequenced by the method of Sanger et al., *Proc. Natl. Acad. Sci. USA.* 1977, 74:5463-5467 or Messing et al., *Nucleic Acids Res.* 1981, 9:309), or by the method of Maxam et al. (*Methods in Enzymology* 1980, 65:499). Host cells are transformed with the above-described expression vectors and cultured in conventional nutrient media modified as appropriate for the promoter utilized.

Chemical Definitions

The term 'alkyl' refers to a straight or branched $C_1$-$C_{20}$ hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1,1-dimethylethyl (t-butyl). The alkyls used herein are preferably $C_1$-$C_5$ alkyls.

The term "alkenyl" refers to a $C_2$-$C_{20}$ aliphatic hydrocarbon group containing at least one carbon-carbon double bond and which may be a straight or branched chain, e.g., ethenyl, 1-propenyl, 2-propenyl iso-propenyl, 2-methyl-1-propenyl, 1-butenyl, 2-butenyl.

The term "cycloalkyl" denotes an unsaturated, non-aromatic mono- or multicyclic hydrocarbon ring system such as cyclopropyl, cyclobutyl, cyclopentyl, cyclohexyl. Examples of multicyclic cycloalkyl groups include perhydronapththyl, adamantyl and norbornyl groups bridged cyclic group or sprirobicyclic groups, e.g., spiro (4,4) non-2-yl.

The term "cycloalkalkyl" refers to a cycloalkyl as defined above directly attached to an alkyl group as defined above, that results in the creation of a stable structure such as cyclopropylmethyl, cyclobutylethyl, cyclopentylethyl.

The term "alkyl ether" refers to an alkyl group or cycloalkyl group as defined above having at least one oxygen incorporated into the alkyl chain, e.g., methyl ethyl ether, diethyl ether, tetrahydrofuran.

The term "alkyl amine" refers to an alkyl group or a cycloalkyl group as defined above having at least one nitrogen atom, e.g., n-butyl amine and tetrahydrooxazine.

The term "aryl" refers to aromatic radicals having in the range of about 6 to about 14 carbon atoms such as phenyl, naphthyl, tetrahydronapthyl, indanyl, biphenyl.

The term "arylalkyl" refers to an aryl group as defined above directly bonded to an alkyl group as defined above, e.g., —$CH_2C_6H_5$, and —$C_2H_4C_6H_5$.

The term "heterocyclic" refers to a stable 3- to 15-membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized;

and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl.

The heterocyclic ring radical may be attached to the main structure at any heteroatom or carbon atom that results in the creation of a stable structure.

The term "heteroaryl" refers to a heterocyclic ring wherein the ring is aromatic.

The term "heteroarylalkyl" refers to heteroaryl ring radical as defined above directly bonded to alkyl group. The heteroarylalkyl radical may be attached to the main structure at any carbon atom from alkyl group that results in the creation of a stable structure.

The term "heterocyclyl" refers to a heterocylic ring radical as defined above. The heterocyclyl ring radical may be attached to the main structure at any heteroatom or carbon atom that results in the creation of a stable structure.

The term "heterocyclylalkyl" refers to a heterocylic ring radical as defined above directly bonded to alkyl group. The heterocyclylalkyl radical may be attached to the main structure at carbon atom in the alkyl group that results in the creation of a stable structure.

The substituents in the 'substituted alkyl', 'substituted alkenyl' 'substituted alkynyl' 'substituted cycloalkyl' 'substituted cycloalkalkyl' 'substituted cyclocalkenyl' 'substituted arylalkyl' 'substituted aryl' 'substituted heterocyclic ring', 'substituted heteroaryl ring,' 'substituted heteroarylalkyl', or 'substituted heterocyclylalkyl ring', may be the same or different with one or more selected from the groups hydrogen, hydroxy, halogen, carboxyl, cyano, amino, nitro; oxo (=O), thio (=S), or optionally substituted groups selected from alkyl, alkoxy, alkenyl, alkynyl, aryl, arylalkyl, cycloalkyl, aryl, heteroaryl, heteroarylalkyl, heterocyclic ring, —CO-OR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$(O)R$^y$—, —NR$^x$C(S)R$^y$ —NR$^x$C(S)NR$^y$R$^z$, —SONR$^x$R$^y$—, —SO$_2$NR$^x$R$^y$—, —OR$^x$C(O)NR$^y$R$^z$, —OR$^x$C(O)OR$^y$—, —OC(O)R$^x$, —OC(O)NR$^x$R$^y$, —R$^x$NR$^y$R$^z$, —R$^x$R$^y$R$^z$, —R$^x$CF$_3$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, —ONO$_2$, wherein R$^x$, R$^y$ and R$^z$ in each of the above groups can be hydrogen atom, substituted or unsubstituted alkyl, haloalkyl, substituted or unsubstituted arylalkyl, substituted or unsubstituted aryl, substituted or unsubstituted cycloalkyl, substituted or unsubstituted cycloalkalkyl substituted or unsubstituted heterocyclic ring, substituted or unsubstituted heterocyclylalkyl, substituted or unsubstituted heteroaryl or substituted or unsubstituted heteroarylalkyl.

The term "halogen" refers to radicals of fluorine, chlorine, bromine and iodine.

Toxic Gain of Function

In one particular embodiment, the invention relates to the use of specific pharmacologic chaperones for a lysosomal enzyme to increase the level of appropriate protein trafficking and decrease the level of mutant enzyme accumulation. This in turn, can be used to treat neurological conditions associated with a mutation or mutations in the enzyme, including forms of lysosomal storages diseases in which the mutation on one or both alleles yields enzymes which are conformational mutations but which also have mutations in functional domains, abrogating enzyme activity. This embodiment is exemplified herein by the effect of a specific pharmacological chaperone on a mutant Gba found in a neurological form of Gaucher disease where there was no functional Gba present. The chaperone increased the level of Gba protein trafficking from the ER, and restored proper ubiquitination of the mutant protein. This effect was not foreseeable from the prior work on ASSC rescue of protein function.

Protein aggregation, such as mutant Gba accumulation, in the CNS is particularly dire since neurons are unable to regenerate following neurodegeneration or apoptosis that arises from neuronal stress associated with the toxic accumulation. Thus, the presence of homozygous or heterozygous mutations is sufficient to cause mutant protein aggregation or accumulation in neurons and cell stress, ultimately leading to cell death. Numerous reports have been published linking protein aggregation in the CNS to pathology.

Therefore, in one embodiment, the present invention is based, on the concept that CNS pathology in lysosomal storage diseases, and other neurological disorders associated with mutations in lysosomal enzymes can be explained, in part, by toxic accumulation of mutant, misfolded enzymes in neurons, and that a specific pharmacological chaperone approach can reverse this effect. The toxic effect also is dependent upon the protein's function, the effects of the mutation on the protein's function and stability, and whether loss or reduction of protein function is more or less deleterious than the toxic affects of protein accumulation and/or aggregation. Accordingly, increasing trafficking of the protein from the ER using a specific pharmacological chaperone can alleviate disease pathology by reducing the toxic effects of protein accumulation/aggregation, even without necessarily restoring protein function.

It follows that specific pharmacological chaperones could potentially be used to treat any disease in which a significant contributor to disease pathology is toxic accumulation of protein and/or protein aggregation, including that associated with neurodegenerative diseases, especially lysosomal storage diseases with neurological involvement such as Gaucher disease, and other neurological risks factors, disorders, or conditions associated with mutations in lysosomal enzymes, such as Parkinson's disease.

As indicated above, other types of neurological disease that may be associated with a dysfunctional lysosomal enzyme and thus may be treated by pharmacological chaperones are Alzheimer's, Amyotrophic Lateral Sclerosis, Canavan's, Creutzfeldt-Jakob, Huntington's, Multiple Sclerosis, Pick's Disease, and Spinocerebellar Atrophy.

Accordingly, a treatment method that increases mutant enzyme transport from the ER, and/or increases enzyme activity, is beneficial in mitigating the neuronopathic effects associated with the lysosomal storage disease or other associated neurological diseases that are linked with mutations in lysosomal enzymes. Even in the absence of increasing enzyme activity (i.e., restoring loss of function), and reducing the accumulation of substrate, proper trafficking of mutant enzyme has beneficial effects on the neuron such as (i) alleviating cell stress on the ubiquitin/proteasome degradation pathway for normal proteins; or (ii) reducing the unfolded protein response caused by ER stress, thus improving pathologies such as e.g., α-synuclein aggregation in Parkinson's patients having mutations in Gba. Support for these effects is provided directly below.

Cell stress. It is well established that accumulation or aggregation of numerous misfolded proteins in a cell leads to cell stress. This stress is sometimes correlated with increased amounts of polyubiquitin, a cell "stress" protein. Ubiquitin-protein conjugates have revealed that ubiquitin is a component of many of the filamentous inclusion bodies characteristic of neurodegenerative diseases, suggesting activation of a common neuronal response in this type of disease process (Lowe et al., *Neuropathol Appl Neurobiol.* 1990; 16: 281-91). For example, genetic studies, including identification of mutations in genes associated with familial Parkinson's (including α-synuclein), and the presence of proteinaceous cytoplasmic inclusions in spared dopaminergic nigral neurons in sporadic cases of Parkinson's have suggested an important role for ubiquitin-proteasome system and aberrant protein degradation (Betarbet et al., *Exp Neurol.* 2005; 191 Suppl 1:S17-27).

In addition, in vivo and in vitro studies have linked aggregated α-synuclein and oxidative stress to a compromised ubiquitin-proteasome system and Parkinson's disease pathogenesis. Moreover, structural and functional defects in 26/20S proteasomes with accumulation and aggregation of potentially cytotoxic abnormal proteins have been identified in the substantia nigra pars compacta of patients with sporadic Parkinson's disease (McKnaught et al., *Ann Neurol.* 2003; 53 Suppl 3:S73-84). Specifically, mutations in α-synuclein that cause the protein to misfold and resist proteasomal degradation cause familial Parkinson's. Thus, a defect in protein handling appears to be a common factor in sporadic and the various familial forms of PD. This same conclusion was drawn from experiments in which a combination of a proteasome inhibitor with agents that induce protein misfolding were added to a culture of dopaminergic neurons (Mytilineou et al., *J Neural Transm.* 2004; 111(10-11):1237-51). Preferential loss of dopamine neurons and cell death is markedly increased when the two are combined.

Further, it has been reported that ubiquitinated protein aggregates were found in patient cells for some lysosomal storage diseases, including Gaucher disease (Asmarina et al., *Eur. J. Biochem.* 2003; Supplement 1; abstract no. P3.7-08). These cells also displayed altered gene expression patterns for genes related to the ubiquitin/proteasome pathway.

An alternate theory for disruptions in neuronal homeostasis in LSDs with CNS involvement is due to suppression of the ubiquitin/proteasome pathway by the accumulated enzymes (Rocca et al., *Molecular Biology of the Cell.* 2001; 12: 1293-1301). For example, it has been found that one of the mechanisms of toxicity associated with α-synuclein aggregation is proteasomal inhibition, which occurs in many neurodegenerative processes. Specifically, it was shown that aggregated α-synuclein inhibits proteasomal function by interacting with S6', a subunit of the proteasome (Snyder et al., *J Mol. Neurosci.* 2004; 24(3):425-42). Proteasomal function is decreased in brains of subjects with Parkinson's disease as well as in brains from individuals and animals lacking parkin, which is an E3 ubiquitin ligase and part of the ubiquitin proteasomal system. Protein aggregation and associated proteasomal inhibition has also been linked to inflammation (Li et al., *Int. J. Biochem. Cell Biol.* 2003; 35: 547-552). It has been proposed that an imbalance between molecular chaperones and damaged/denatured/misfolded proteins, leading to accumulation of the latter, can result in senescence, inhibition of the proteasome (leading to apoptosis), or necrosis, depending on the severity of the imbalance (Soti et al., *Aging Cell.* 2003; 2: 39-45). This hypothesis is referred to as the "toxic protein accumulation hypothesis." Since α-synuclein monomers are thought to be degraded by the proteasomes and oligomer formation is concentration dependent, this could lead to an accumulation and oligomerization of α-synuclein. The accumulation of both mutant Gba and α-synuclein (the latter due to loss of Gba activity) would exacerbate this effect on the proteasomes, and deficient Gba may also impair any increase in the autophagic response by lysosomes that occurs to compensate for the deficiency of the proteasome degradation pathway.

ER stress. In addition to the above-referenced discussion, continued accumulation of misfolded proteins in the lumen of the ER creates an ER stress response, which, in turn, elicits the "unfolded protein response" (UPR). The UPR is a quality control cell stress response that results from inhibition of protein synthesis, such as by oxidative stress, or retention of mutant proteins in the ER that are unable to fold. Without this response, the ER becomes engorged with misfolded, unstable proteins which can result in cell death via apoptosis (Gow et al., *NeuroMolecular Med.* 2003; 4: 73-94).

It has also been shown that Gba interacts with the Rhyanodine receptor in the ER to disturb $Ca^{2+}$ homeostasis, leading to impaired protein folding and a UPR, ER-stress induced apoptosis and mitochondrial-directed cell death due to an increase in cytosolic $Ca^{2+}$ (Korkotian et al., *J Biol. Chem.* 1999. 274(31): 21673-8; Lloyd-Evans et al., *J Biol. Chem.* 2003. 278(26): 23594-9; Pelled et al., *Neurobiol Dis.* 2005. 18(1): 83-8).

Autophagy. In addition to degrading lipids, lysosomes are responsible for degrading aggregated proteins (discussed further below). This process, called autophagy, is an intracellular bulk degradation process through which a portion of the cytoplasm is delivered to lysosomes to be degraded by lysosomal enzymes. Such enzymes include proteases (cathepsins) which cleave peptide bonds, phosphatases, which remove covalently bound phosphates, nucleases, which cleave DNA/RNA, lipases, which cleave lipid molecules, and carbohydrate-cleaving enzymes. Aggregated proteins, including mutated lysosomal enzymes, can cause activation of a conspicuous autophagic response leading to long-lasting degenerative changes in neurons. Many neurons in CNS disorders, including amyotrophic lateral sclerosis (ALS), exhibit irregular vesicular trafficking and autophagic responses.

It is possible that excessive autophagic-lysosomal vacuolation can cause neuronal death. Over activation of the autophagic response, especially in combination with inhibition of the proteasome pathway as a compensatory mechanism, by accumulated mutant proteins is one hypothesis for a link between accumulated mutant lysosomal enzymes and neurodegeneration, especially in Alzheimer's disease.

Pathologic Loss of Function

In addition to restoring proper trafficking of lysosomal enzymes, specific pharmacological chaperone restoration of mutant enzyme activity will be beneficial in patients harboring a destabilizing mutation(s) in one or both alleles which reduces the amount of functional enzyme (e.g., Gba) at its native location (e.g., the lysosome) due to inefficient folding and trafficking. Even a small loss of function can lead to pathologies such as substrate accumulation or aggregation, which can result in seeding of other pathologic aggregates.

Therefore, in one embodiment, the present invention provides methods for improving neurological disorders associated with mutant lysosomal enzyme proteins by increasing reduced activity of the enzymes which will, in turn, (i) increase lysosomal degradation of substrates, aggregated proteins or fragments; (ii) decrease neuronal apoptosis or necrosis; and (iii) prevent alteration of the phospholipid "balance" in cell membranes (discussed directly below).

Possible explanations postulated to explain the neuronal loss or neuropathy in Gaucher disease can be explained by the loss of Gba activity associated with the mutations. Loss of activity causes the accumulation of ceramide, such as the GluCer, in cells with deficient Gba. This has been shown to cause apoptosis in cultured hippocampal CA2-4 neuron cells, due to an increase in intracellular calcium, and an increase in sensitivity to calcium-mediated cell death. Dopaminergic neurons have also been shown to undergo apoptosis after ceramide-induced damage.

Second, high levels of the toxic compound glucosylsphingosine, also a substrate of Gba, have been observed in organs from lethal null allele Gaucher mice. Glucosylsphingosine also is elevated in tissues from patients having all three types of Gaucher disease. Although brain levels are elevated only in those patients with neuronal involvement using current methods of detection (Sidransky, *Mol. Gen. Metabol.* 2004; 83: 6-15), small amounts of accumulation not detectable using current methods could still affect protein folding and also impair protein trafficking by affecting lipid raft composition (discussed infra).

Third, membrane phospholipid content affects the activity of Gba in cells. Namely, negatively charged phospholipids enhance Gba activity, and positively charged phospholipids such as phosphotidylcholine (PC) do not. Therefore, a mechanism where decreased Gba in Gaucher disease activates an enzyme involved in the synthesis of PC, thereby increasing PC, may cause a further reduction in Gba (Wong et al., supra). In addition, elevated ceramide may hinder axonal transport of α-synuclein, favoring aggregation and Lewy body formation. Neurons presumably require α-synuclein for function. Since α-synuclein binds PC poorly, axonal transport vesicles that are comprised primarily of PC may not be as efficient as vesicles comprised of acidic phospholipids (Wong et al., supra).

Further, as discussed above, lysosomes are involved in clearing aggregates involved in numerous CNS disorders by autophagy. Autophagy is particularly relevant in neurons, since loss of autophagy causes neurodegeneration even in the absence of any disease-associated mutant proteins (Hara et al., *Nature.* online publication Apr. 19, 2006). Induction of the lysosomal autophagic system, in a protective effort to eliminate altered intracellular components occurs during oxidative stress (Kiffin et al., *Antioxid Redox Signal.* 2006; 8(1-2):152-62).

As one example, α-synuclein oligomers. One group reported an interaction between glucosylceramide containing gangliosides and α-synuclein in lysosomes in human brain homongenates (Schlossmacher et al., *New Eng J. Med.* 2005; 352: 730). In Gaucher patients with Parkinson's, Gba colocalized with α-synuclein in Lewy bodies (Wong et al., *Mol. Genet. Metabol.* 2004; 38: 192-207). These results support that processing of α-synuclein occurs within lysosomes, and provides a biochemical link between decreased Gba activity and synucleinopathy in Parkinson's disease.

In addition, autophagy is essential for the elimination of aggregated forms of mutant huntingtin and ataxin-1 from the cytoplasmic compartment (Iwata et al., *Proc Natl Acad Sci USA.* 2005; 102(37):13135-40). Autophagy also plays the major role in clearing of cells from protein aggregates in Amyotrophic Lateral Sclerosis, Alzheimer's disease, Parkinson's disease, Huntington Disease and other polyglutamine expansion disorders (Merlin et al., *Int J Hyperthermia.* 2005; 21(5):403-19). Thus, deficiencies in lysosomal hydrolases would adversely affect the autophagic response to toxic accumulation of proteins (including accumulated lysosomal proteins themselves)

Substrate accumulation and endocytic trafficking defects. Accumulation of cellular substrates, such as the sphingolipids and cholesterol in lysosomal diseases, especially those involving the CNS, has been associated with disruptions in endocytic trafficking of proteins and lipids. This may occur because of the disruption of rab (ras in the brain) proteins, which are membrane associated proteins that localize to discrete subcellular compartments and are associated with protein trafficking. The rab disruption causes sequestering by membrane-associated proteins into "lipid rafts." Lipid rafts are membrane microdomains enriched in sphingolipids (sphingomyelin and phosphotidylcholine) and cholesterol. They have been suggested to serve as platforms for various cellular events, including signaling and membrane trafficking. In particular, lipid rafts stabilize the association of GPI-anchored proteins within the ER membrane and are directly involved in protein conformation and also direct the lipids or lipid-associated proteins entering the cell to the appropriate compartment via endosomes. Therefore, the accumulation of lipid rafts in membranes of endosomes and lysosomes in e.g., lysosomal storage diseases, due to decreased lipid hydrolase activity, could alter intracellular sorting of glycosphingolipids (which are already accumulated), and lipid-associated proteins which enter the cell (Pagano et al., *Philos Trans R Soc Lond B Biol Sci.* 2003; 358: 885-91).

This mis-sorting hypothesis is supported by recent findings in mucopolysaccharidoses (MPSs), where it was demonstrated that two different accumulated substrates, $G_{M2}$ and $G_{M3}$ gangliosides, accumulated in the same neurons, but were consistently located in separate populations of cytoplasmic vesicles (McGlynn et al., *Comp Neurol.* 2004; 480: 415-26). These authors hypothesized that co-sequestration in individual neurons suggests the presence of defects in the composition, trafficking, and/or recycling of lipid raft components, leading to new mechanisms to explain neuronal dysfunction in MPS disorders.

Studies of mouse models for Gaucher disease also suggest that reduced Gba activity more generally disrupts glycosphingolipid catabolism leading to accumulation of more complex species (gangliosides). Accumulation of gangliosides can results in dystonia and parkinsonism in humans (Roze et al., *Movement Disorders.* 2005; 20(10): 1366-1369). A mouse model that accumulates $G_{M2}$ ganglioside also accumulated α-synuclein (Suzuki et al., *Neuroreport.* 2003; 14(4):551-4. Such accumulation of gangliosides can also lead to α-synuclein accumulation, as well as neuronal death through the UPR pathways (Lee et al., *J Biol. Chem.* 2002. 277(1): 671-8). Further, as recited above, is has been shown that sphingolipids can function as a seed for the formation of α-synuclein aggregates.

These mechanisms of neurotoxicity as a result of accumulation of lipids partially can explain the neuropathology of Gaucher disease, since there is a loose correlation between Gba activity and Gaucher disease severity. This correlation works to differentiate the three major disease types (I-III), although there is overlap and the correlation is weak within the individual types. Patients who are heterozygous normal for Gba do not experience significant accumulation of lipids, because there is some amount of active Gba produced by the normal allele. However, even accumulation of small amounts of GluCer can disrupt ER calcium homeostasis and impair protein folding, (described above), or possibly even seed α-synuclein aggregation by some mechanism.

In view of the foregoing, the use of specific pharmacological chaperones according to the present invention is advantageous over enzyme replacement therapy (ERT) and substrate reduction therapy (SRT), since the former must be administered directly into the brain via a catheter, and since neither address the problems of toxic accumulation of the mutant lysosomal enzymes themselves, i.e., mutant Gba. Therefore, these treatments are less effective than a treatment than can reduce mutant protein accumulation, or enhance and/or restore protein function (thereby reducing substrate accumulation) or both.

Mutant Lysosomal Enzymes and Specific Pharmacological Chaperones

Following is a table which lists lysosomal enzymes and specific pharmacological chaperones for those lysosomal enzymes which can be used to treat individuals having mutations in the enzymes and who have a resultant neurological condition or disorder, or are at risk of developing a neurological condition or disorder.

| LYSOSOMAL ENZYME | SPECIFIC PHARMACOLOGICAL CHAPERONE |
|---|---|
| α-Glucosidase GenBank Accession No. Y00839 | 1-deoxynojirimycin (DNJ) α-homonojirimycin castanospermine |
| Acid β-Glucosidase (glucocerebrosidase) GenBank Accession No. J03059 | isofagomine C-benzyl isofagomine and derivatives N-alkyl (C9-12)-DNJ Glucoimidazole (and derivatives) C-alkyl-IFG (and derivatives) N-alkyl-β-valeinamines Fluphenozine calystegines $A_3$, $B_1$, $B_2$ and $C_1$ |
| α-Galactosidase A GenBank Accession No. NM000169 | 1-deoxygalactonojirimycin (DGJ) α-allo-homonojirimycin α-galacto-homonojirimycin β-1-C-butyl-deoxynojirimycin calystegines $A_2$ and $B_2$ N-methyl calystegines $A_2$ and $B_2$ |
| Acid β-Galactosidase GenBank Accession No. M34423 | = |
| Galactocerebrosidase (Acid β-Galactosidase) GenBank Accession No. D25283 | 4-epi-isofagomine 1-deoxygalactonojirimycin |
| Acid α-Mannosidase GenBank Accession No. U68567 | 1-deoxymannojirimycin Swainsonine Mannostatin A |
| Acid β-Mannosidase GenBank Accession No. U60337 | 2-hydroxy-isofagomine |
| Acid α-L-fucosidase GenBank Accession No. NM_000147 | 1-deoxyfuconojirimycin β-homofuconojirimycin 2,5-imino-1,2,5-trideoxy-L-glucitol 2,5-deoxy-2,5-imino-D-fucitol 2,5-imino-1,2,5-trideoxy-D-altritol |
| α-N-Acetylglucosaminidase GenBank Accession No. U40846 | 1,2-dideoxy-2-N-acetamido-nojirimycin |
| α-N-Acetylgalactosaminidase GenBank Accession No. M62783 | 1,2-dideoxy-2-N-acetamido-galactonojirimycin |
| β-Hexosaminidase A GenBank Accession No. NM_000520 | 2-N-acetylamino-isofagomine 1,2-dideoxy-2-acetamido-nojirimycin nagstain |
| β-Hexosaminidase B GenBank Accession No. NM_000521 | 2-N-acetamido-isofagomine 1,2-dideoxy-2-acetamido-nojirimycin nagstain |
| α-L-Iduronidase GenBank Accession No. NM_000203 | 1-deoxyiduronojirimycin 2-carboxy-3,4,5-trideoxy-piperidine |
| β-Glucuronidase GenBank Accession No. NM_000181 | 6-carboxy-isofagomine 2-carboxy-3,4,5-trideoxy-piperidine |
| Sialidase GenBank Accession No. U84246 | 2,6-dideoxy-2,6, imino-sialic acid Siastatin B |
| Iduronate sulfatase GenBank Accession No. AF_011889 | 2,5-anhydromannitol-6-sulphate |
| Acid sphingomyelinase GenBank Accession No. M59916 | desipramine, phosphatidylinositol-4,5-diphosphate |

In one specific embodiment, following are some specific pharmacological chaperones contemplated by this invention which can be used for treating neurological risk factors, conditions or disorders in which Gba is mutated. Also exemplified are Gba mutations contemplated to be "rescued" by the chaperones.

Gba mutations. The presence of Gba point mutation N370S on at least one allele (heterozygotes) is almost universally associated with type 1 Gaucher disease (Cox, supra). N370S homozygosity is associated with a less severe phenotype than Gba null/N370S heterozygosity (N370S/null), likely due to the residual Gba activity of the homozygotes. In fact, some N370S/N370S patients are asymptomatic throughout most of their life but may be at risk for developing neurological disorders such as Parkinson's. In this case, the Gba mutation would be a risk factor for Parkinson's. Additional point mutations associated with type 1 Gaucher include 84GG, R496H, Q350X, and H162P (Orvisky et al., *Human Mutation*. 2002; 495, 19(4):458-9). In addition, splice-site mutation IVS10+2T→G and IVS10+2T→A were also associated with type I Gaucher disease (Orvisky, supra).

Neuronopathic type 2 Gaucher disease is associated with mutations resulting primarily in two amino acid substitutions, L444P and A456P. L444P homozygosity also is commonly associated with type 3 Gaucher disease, although this mutation has been identified in patients with all three disease types. Other point mutations associated with types 2 and 3 neuronopathic Gaucher disease include D409H (homozygotes) and V349L and D409V (heterozygotes). Patients homozygous for D409H exhibit a unique phenotype that includes hydrocephalus and cardiac valve and aortic calcification in addition to the neurological involvement. The latter two point mutations, V349L and D409V, result in Gba that is catalytically defective. Other mutations identified in type 2 or 3 disease are K198E, K198T, Y205C, F251L, I402F, and splice-site mutation IVS10+2T→A (Orvisky et al., supra; and Lewin et al., *Mol Genet Metab*. 2004; 81(0:70-3). Patients and knockout mice lacking any Gba activity die shortly after birth due to dehydration, since ceramide is essential for skin cutaneous integrity (Liu et al., *Proc. Natl. Acad. Sci. USA*. 1998; 95: 2503-08).

Chaperones for Gba. Isofagomine (IFG; (3R,4R,5R)-5-(hydroxymethyl)-3,4-piperidinediol) refers to a compound having the following structure:

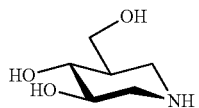

IFG has a molecular formula of $C_6H_{13}NO_3$ and a molecular weight of 147.17. This compound is further described in U.S. Pat. Nos. 5,844,102 to Sierks et al., and 5,863,903, to Lundgren et al.

C-benzyl-IFG, refers to a compound having the following structure:

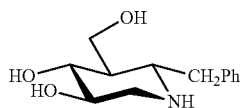

Other chaperones for Gba include glucoimidazole, polycyclohexanyl, and hydroxyl piperidine derivatives, which are described in pending U.S. published applications 2005/0130972 and 2005/0137223, and corresponding PCT publications WO 2005/046611 and WO 2005/046612, all filed on Nov. 12, 2004 and incorporated herein by reference. Glucoimidazole and derivatives are represented by the following chemical structure:

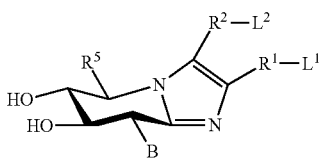

wherein B is selected from the group consisting of hydrogen, hydroxy, acetamino, and halogen;

$R^1$ and $R^2$ optionally present are short, flexible linkers linear length of about 6 Å to about 12 Å, preferably about 9 Å. $R^1$ and $R^2$ can also be independently selected from the group consisting of $C_2$-$C_6$ substituted or unsubstituted alkyl optionally interrupted by one or more moieties chosen from the group consisting of NH, NHCOO, NHCONH, NHCSO, NHCSNH, CONH, NHCO, $NR^3$, O, S, $S(O)_m$ and —$S(O)_m$ $NR^3$; $C_2$-$C_6$ substituted or unsubstituted alkenyl optionally interrupted by one or more moieties chosen from the group consisting of NH, NHCOO, NHCONH, NHCSO, NHCSNH, CONH, NHCO, $NR^3$, O, S, $S(O)_m$ and —$S(O)_m$ $NR^3$; $C_2$-$C_6$ substituted or unsubstituted alkynyl optionally interrupted by one or more moieties chosen from the group consisting of NH, NHCOO, NHCONH, NHCSO, NHCSNH, CONH, NHCO, $NR^3$, O, S, $S(O)_m$ and —$S(O)_m$ $NR^3$, whereas m is 1 or 2, and $R^3$ is independently selected from each occurrence from the groups consisting of hydrogen substituted or unsubstituted alkyl, substituted or unsubstituted alkenyl; substituted or unsubstituted alknyl; substituted or unsubstituted cycloalkyl, substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocyclyalkyl; substituted or unsubstituted heteroarylalkyl; and pharmaceutically acceptable salts and prodrugs thereof.

In addition, $R^1$-$L^1$ or $R^2$-$L^2$ can be a hydrogen, if either $R^2$-$L^2$ or $R^1$-$L^1$ is other than a hydrogen, respectively.

$R^5$ represents a hydrogen, hydroxy, or hydroxylmethyl;

$L^1$ and $L^2$ are lipophilic groups selected from the group consisting of $C_3$-$C_{12}$ substituted or unsubstituted alkyl, substituted or unsubstituted alkenyl substituted or unsubstituted alkynyl; substituted or unsubstituted cycloalkyl, substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocycloalkyl; substituted or unsubstituted heteroarylalkyl.

In specific embodiments, GIZ compounds include (5R,6R,7S,8S)-5-hydroxymethyl-2-octyl-5,6,7,8-tetrahydroimidazo[1,2-a]pyridine-6,7,8-triol and (5R,6R, 7S, 8 S)-5-Hydroxymethyl-2-(3,3-dimethylbutyl)-5,6,7,8-tetrahydroimidazo[1,2-a]pyridine-6,7,8-triol.

Polyhydroxylcycloalkyl (PHCA) derivatives contemplated for use in the present invention include compounds represented by the following chemical structure:

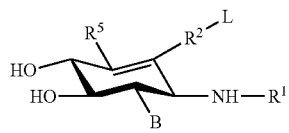

wherein B is selected from the group consisting of hydrogen, hydroxy, N-acetamino, and halogen.

$R^1$ is independently selected for each occurrence from the group consisting of hydrogen; substituted or unsubstituted alkyl, substituted or unsubstituted alkenyl, substituted or unsubstituted alkynyl, substituted or unsubstituted cycloalkyl substituted or unsubstituted cycloalkenyl, substituted or unsubstituted aryl, substituted or unsubstituted arylalkyl, substituted or unsubstituted heteroaryl, substituted or unsubstituted heterocyclic, substituted or unsubstituted heterocyclyalkyl, substituted or unsubstituted heteroarylalkyl, —$C(O)R^3$ and —$S(O)_mR^3$, whereas m is 1 or 2, and $R^3$ is independently selected for each occurrence from the groups consisting of hydrogen, substituted or unsubstituted alkyl, substituted or unsubstituted alkenyl; substituted or unsubstituted alknyl; substituted or unsubstituted cycloalkyl, substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocyclyalkyl; substituted or unsubstituted heteroarylalkyl, and —C(O) attached to a $C_1$-$C_6$ substituted or unsubstituted alkyl.

$R^2$ optionally present is a short, flexible linker linear length of about 6 Å to about 12 Å, preferably, about 9 Å. $R^2$ can also be selected from the group consisting of $C_2$-$C_6$ substituted or unsubstituted alkyl optionally interrupted by one or more moieties chosen from the group consisting of NH, NHCOO, NHCONH, NHCSO, NHCSNH, CONH, NHCO, $NR^3$, O, S, $S(O)_m$ and —S(O). $NR^3$; $C_2$-$C_6$ substituted or unsubstituted alkenyl optionally interrupted by one or more moieties chosen from the group consisting of NH, NHCOO, NHCONH, NHCSO, NHCSNH, CONH, NHCO, $NR^3$, O, S, $S(O)_m$ and —S(O). $NR^3$; $C_2$-$C_6$ substituted or unsubstituted alkynyl optionally interrupted by one or more moieties chosen from the group consisting of NH, NHCOO, NHCONH, NHCSO, NHCSNH, CONH, NHCO, $NR^3$, O, S, $S(O)_m$ and —S(O).

$NR^3$, whereas m is 1 or 2, and $R^3$ is independently selected for each occurrence from the groups consisting of hydrogen, substituted or unsubstituted alkyl, substituted or unsubstituted alkenyl; substituted or unsubstituted alknyl; substituted or unsubstituted cycloalkyl, substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocyclyalkyl; substituted or unsubstituted heteroarylalkyl, and —C(O) attached to a $C_1$-$C_6$ substituted or unsubstituted alkyl; and pharmaceutically acceptable salts and prodrugs thereof.

L is a lipophilic group selected from the group consisting of $C_3$-$C_{12}$ substituted or unsubstituted alkyl, substituted or unsubstituted alkenyl, substituted or unsubstituted alkynyl; substituted or unsubstituted cycloalkyl; substituted or unsubstituted cycloalkenyl; substituted or unsubstituted aryl; substituted or unsubstituted arylalkyl; substituted or unsubstituted heteroaryl; substituted or unsubstituted heterocyclic; substituted or unsubstituted heterocycloalkyl; substituted or unsubstituted heteroarylalkyl.

Hydroxylpiperidine derivatives contemplated for use in the present invention where Gba is mutated are represented by the following chemical structure.

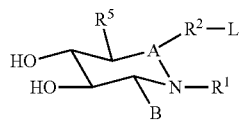

wherein A represents a carbon or nitrogen;

B is a hydrogen, hydroxyl, N-acetamide or a halogen;

$R^1$ is a hydrogen, substituted or unsubstituted: alkyl, alkenyl, alkynyl, cycloalkyl, cycloalkenyl, aryl, arylalkyl, heteroaryl, heterocyclic, heterocyclyalkyl, or heteroarylalkyl; —C(O)$R^3$ or —S(O)$_m R^3$. Preferably, R' comprises H or an organic moiety having 1-12 carbon atoms.

$R^2$ is an optional short, flexible linker with a linear length of from about 6 Å to about 12 Å. Alternatively, $R^2$ is a $C_1$-$C_6$ substituted or unsubstituted: alkyl, alkenyl, or alkynyl optionally interrupted by one or more moieties chosen from the group consisting of NH, NHCOO, NHCONH, NHCSO, NHCSNH, CONH, NHCO, $NR^3$, O, S, S(O)$_m$ and —S(O)$_m$ $NR^3$.

$R^3$ is of hydrogen, or a substituted or unsubstituted: alkyl, alkenyl; alknyl; cycloalkyl, cycloalkenyl; aryl; arylalkyl; heteroaryl; heterocyclic; heterocyclyalkyl; or heteroarylalkyl. Preferably, $R^3$ comprises H or an organic moiety having 1-12 carbon atoms, or more preferably 1-6 carbon atoms.

m is 1 or 2, and $R^5$ is a hydrogen, hydroxyl, or hydroxymethyl.

L is a lipophilic group having 1-12 carbon atoms comprising a substituted or unsubstituted: alkyl, alkenyl, alkynyl; cycloalkyl, cycloalkenyl; aryl; arylalkyl; heteroaryl; heterocyclic; heterocycloalkyl; or heteroarylalkyl.

In specific embodiments, hydroxylpiperidene compounds contemplated for use in the present invention include but are not limited to the following: (3R,4R,5R,6S/6R)-5-(hydroxy methyl)-6-n-butyl-3,4-dihydroxypiperidine; (3R,4R,5R,6S/6R)-5-(hydroxy methyl)-6-n-hexyl-3,4-dihydroxypiperidine; (3R,4R,5R,6S/6R)-5-(hydroxy methyl)-6-n-heptyl-3,4-dihydroxypiperidine; (3R,4R,5R,6S/6R)-5-(hydroxy methyl)-6-n-octyl-3,4-dihydroxypiperidine; (3R,4R,5R,6S/6R)-5-(hydroxy methyl)-6-n-nonyl-3,4-dihydroxypiperidine; (3R,4R,5R,6S/6R)-5-(hydroxy methyl)-6-benzyl-3,4-dihydroxypiperidine.

Still other chaperones for Gba are described in U.S. Pat. No. 6,599,919 to Fan et al., and include calystegine $A_3$, calystegine $A_5$, calystegine $B_1$, calystegine $B_2$, calystegine $B_3$, calystegine $B_4$, calystegine $C_1$, N-methyl-calystegine $B_2$, DMDP, DAB, castanospermine, 1-deoxynojirimycin, N-butyl-deoxynojirimycin, 1-deoxynojirimycin bisulfite, N-butyl-isofagomine, N-(3-cyclohexylpropyl)-isofagomine, N-(3-phenylpropyl)-isofagomine, and N-[(2E,6Z,10Z)-3,7,11-trimethyldodecatrienyl]-isofagomine.K In another specific embodiment following are specific pharmacological chaperones including 1-deoxynojirimycin (DNJ; 1,5-imino-1,5-dideoxy-D-glucitol-CAS No. 19130-96-2) and derivatives which can be used for treating neurological risk factors, conditions or disorders in which the lysosomal enzyme α-glucosidase (Gaa) is mutated.

Exemplary mutations of Gaa include the following: D645E (Lin et al., *Zhonghua Min Guo Xiao Er Ke Yi Xue Hui Za Zhi*. 1996; 37(2):115-21); D645H (Lin et al., *Biochem Biophys Res Commun*. 1995 17; 208(2):886-93); R224W, S619R, and R660H (New et al. *Pediatr Neurol*. 2003; 29(4):284-7); T1064C and C2104T (Montalvo et al., *Mol Genet Metab*. 2004; 81(3):203-8); D645N and L901Q (Kroos et al., *Neuromuscul Disord*. 2004; 14(6):371-4); G219R, E262K, M408V (Fernandez-Hoj as et al., *Neuromuscul Disord*. 2002; 12(2): 159-66); G309R (Kroos et al., *Clin Genet*. 1998; 53(5):379-82); D645N, G448S, R672W, and R672Q (Huie et al., *Biochem Biophys Res Commun*. 1998; 27; 244(3):921-7); P545L (Hermans et al., *Hum Mol. Genet*. 1994; 3(12):2213-8); C647W (Huie et al., Huie et al., *Hum Mol. Genet*. 1994; 3(7):1081-7); G643R (Hermans et al., *Hum Mutat*. 1993; 2(4):268-73); M318T (Zhong et al., *Am J Hum Genet*. 1991; 49(3):635-45); E521K (Hermans et al., *Biochem Biop hys Res Commun*. 1991; 179(2):919-26); W481R (Raben et al., *Hum Mutat*. 1999; 13(1):83-4); and L552P and G549R (unpublished data).

Splicing mutants include IVS1AS, T>G, −13 and IVS8+ 1G>A).

Exemplary α-glucosidase chaperones are represented by the following chemical structure:

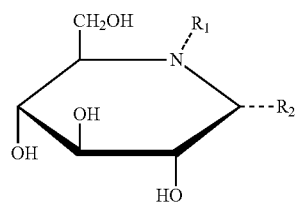

wherein:

$R_1$ is H or a straight or branched alkyl, cycloalkyl, alkenyl, alkylether or alkyl amine containing 1-12 carbon atoms, an aryl, alkylaryl, heteroaryl, or heteroaryl alkyl containing 5-12 ring atoms, where $R_1$ is optionally substituted with one or more —OH, —COOH, —Cl, —F, —CF$_3$, —OCF$_3$, —O—C(=O)N-(alkyl)$_2$; and $R_2$ is H; a straight or branched alkyl, cycloalkyl, alkenyl, or alkylether, containing 1-9 carbon atoms or aryl containing 5-12 carbon atoms, wherein $R_2$ is optionally substituted with —OH, —COOH, —CF$_3$, —OCF$_3$ or a heterocyclic ring;

wherein at least one of $R_1$ and $R_2$ is not H, or a pharmaceutically acceptable salt thereof.

In particular, chaperones for acid α-glucosidase include but are not limited to N-methyl-DNJ, N-ethyl-DNJ, N-propyl-DNJ, N-butyl-DNJ, N-pentyl-DNJ, N-hexyl-DNJ, N-heptyl-DNJ, N-octyl-DNJ, N-nonyl-DNJ, N-methylcyclopropyl-DNJ, and N-methylcyclopentyl-DNJ.

In addition to the nitrogen-substituted DNJ derivatives, other DNJ derivatives useful as chaperones for Gaa include N-benzyl substituted DNJ derivatives and derivatives having a substituent appended to the C-1 carbon adjacent to the ring nitrogen are also preferred compounds of the present invention. Such compounds are described in commonly-owned co-pending application Ser. No. 11/440,473, filed on May 17, 2006.

In yet another embodiment, preferred chaperones for treatment of neurological disorders associated with heterozygous mutations in α-galactosidase (α-Gal A), another lysosomal enzyme, are represented by the following chemical structures:

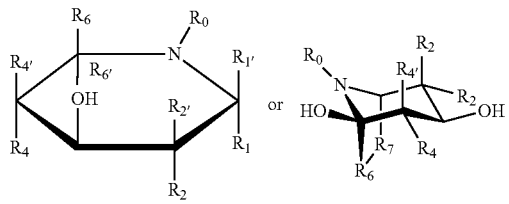

wherein $R_1$ and $R_{1'}$ represent H, OH, or a 1-12 carbon alkyl, hydroxyalkyl or an alkoxyl group;

$R_2$ and $R_{2'}$ independently represent H, LH, or N-acetamido group, or a 1-12 carbon alkyl group;

$R_4$ and $R_{4'}$ independently represent H, OH;

$R_6$ and $R_{6'}$ independently represent H, $CH_2OH$, $CH_3$, or COOH;

$R_7$ represents H or OH:

$R_0$ represents H, methyl, or a straight chain or branched saturated or unsaturated carbon chain containing 9-12 carbon atoms, optionally substituted with a phenyl, hydroxyl or cyclohexyl group.

In a specific embodiment, the chaperone is 1-deoxynojirimycin.

Exemplary α-Gal A mutations associated with Fabry disease include R301Q, L166V, A156V, G272S, and M296I.

Assays

Detection and trafficking of accumulated proteins. Protein accumulation in the ER can be detected and/or visualized and manifests as perinuclear localization in tubulovesicular profiles that co-localize with ER resident proteins such as BiP. These proteins are also reduced or absent at their native location within the cell such as at the cell surface or in another cellular compartment such as the lysosome. Protein accumulation in the cytoplasm can be detected using similar co-localization methods with cytosolic proteins.

Methods for detecting impaired trafficking of lysosomal enzymes are well known in the art. For example, for proteins which are N- and O-glycosylated in the Golgi apparatus, pulse-chase metabolic labeling using radioactively labeled proteins, combined with glycosidase treatment and immunoprecipitation, can be used to detect whether the proteins are undergoing full glycosylation in the Golgi, or whether they are being retained in the ER instead of trafficking to the Golgi for further glycosylation.

Sensitive methods for visually detecting cellular localization of proteins also include fluorescent microscopy using fluorescent proteins or fluorescent antibodies. For evaluation of cell samples, fluorescent antibodies can be used to detect proteins. For detection in manipulated or engineered cells, proteins of interest can be tagged with e.g., green fluorescent protein (GFP), cyan fluorescent protein, yellow fluorescent protein (YFP), and red fluorescent protein, prior to transfection, followed by multicolor and time-lapse microscopy and electron microscopy to study the fate of the proteins in fixed cells and in living cells. For a review of the use of fluorescent imaging in protein trafficking, see Watson et al., *Adv Drug Deliv Rev.* 2005; 57(1):43-61). For a description of the use of confocal microscopy for intracellular co-localization of proteins, see Miyashita et al., *Methods Mol. Biol.* 2004; 261:399-410.

In addition, dual labeling experiments with antibodies to, e.g., LAMP-1 or LysoTracker® for the lysosome (red) (or another stain or marker specific for the lysosome such as fluorescent quantum dots, Cascade blue dextran), and lysosomal enzyme (green), green/red overlap ratios (co-localization) can be used to measure changes in lysosomal enzyme, e.g., enzyme trafficking to the lysosomes (increasing green/red ratio means more enzyme is trafficked to the lysosome). Normal healthy cells with normal endocytic pathways should yield more fluorescence. See also Example 2, infra.

Fluorescence correlation spectroscopy (FCS) is an ultrasensitive and non-invasive detection method capable of single-molecule and real-time resolution (Vukojevic et al., *Cell Mol Life Sci.* 2005; 62(5): 535-50). SPFI (single-particle fluorescence imaging) uses the high sensitivity of fluorescence to visualize individual molecules that have been selectively labeled with small fluorescent particles (Chemy et al., *Biochem Soc Trans.* 2003; 31(Pt 5): 1028-31). For localization of proteins within lipid rafts, see Latif et al., *Endocrinology.* 2003; 144(11): 4725-8). For a review of live cell imaging, see Hariguchi, *Cell Struct Funct.* 2002; 27(5):333-4).

Fluorescence resonance energy transfer (FRET) microscopy is also used to study the structure and localization of proteins under physiological conditions (Periasamy, *J Biomed Opt.* 2001; 6(3): 287-91).

In particular embodiments, detection of α-synuclein in individuals harboring Gba mutations can be done using ELISA or western-blot analysis. LCMS/MS methods and/or TLC can be used to monitor GluCer levels (substrate accumulation).

Ex vivo monitoring of α-synuclein levels and oligomer/monomer ratios, in response to treatment of animals with inhibitors and/or chaperones, can be assessed using brain slice assays.

Ubiquitination assays. In addition, assays to determine the presence and localization of ubiquitin-lysosomal enzyme conjugates can be used to assess toxic gain of function effects of mutations and in response to chaperone treatment. Morphological studies using immunohistochemistry or immunofluorescence to localize these conjugates is one sensitive method of detection. See Example 3, infra. As indicated above, the presence of low levels of ubiquitinated proteins compared with non-stressed cells can be indicative of inhibition of proteasome function.

As another example, a process called AlphaScreen™ (Perkin-Elmer) can be used to detect ubiquitinated proteins. In this model, the GST moiety of a GST-UbCH5a fusion protein is ubiquitinated using biotin-Ubiquitin (bio-Ub). Following ubiquitin activation by E1, in the presence of ATP, bio-Ub is transferred to UbCH5a. In this reaction, UbCH5a acts as the carrier to transfer the bio-Ub to its tagged GST moiety. The protein which becomes biotinylated and ubiquitinated is then captured by anti-GST Acceptor and streptavidin. Donor beads resulting in signal generation. No signal is be generated in the absence of ubiquitination.

In addition, high throughput assays for measuring the activities of the various E3 ubiquitin ligases and E2 conjugation enzymes can be used to determine the increase or decrease in protein ubiquitination (Meso Scale Discovery, Gaithersburg, Md.).

UPR response. ER stress, can be evaluated by determining the expression levels of genes and the proteins encoded by the genes involved in the UPR. Such genes and proteins include those mentioned above, Grp78/BiP, Grp94, and orp150, which are upregulated in the early stages of the UPR. Other proteins involved in the ER stress response include IRE1, PERK, ATF6, and XBP1, which are up-regulated in cells subjected to continued ER stress. Further, prolonged cell stress leads to apoptosis, and thus, upregulation of jun kinase (JNK) and caspases 3, 9 and 12.

The present invention contemplates comparison of expression levels of the aforementioned indicator genes and/or proteins among patients with toxic protein or substrate accumulation or aggregation and healthy individuals.

In another embodiment, the present invention also contemplates evaluating the effect of specific pharmacological chaperones on stressed cells to identify compounds for relieving the cell stress caused by toxic gain of function aggregates. As positive controls, ER stress inducers such as tunicamycin, dithiiothreitol (DTT), lacatcystin, and peroxide can be used to cause accumulation of unfolded proteins in the ER. Tunicamycin inhibits N-linked glycosylation and DTT prevents disulfide bond formation. Lacatcyctin is a proteasome inhibitor. Stress relievers such as cyclohexamide, a protein synthesis inhibitor, can be used as positive controls when evaluating chaperone compounds on stressed cells.

Assays for expression levels include gene expression via microarray analysis. This can be achieved using e.g., Affymetrix U133 gene chip set (human genome) contain such genes (Affymetrix, Santa Clara, Calif.). In addition, this technique has been used by others. For example, microarray analysis of RNA collected from multiple time points following 6-hydroxydopamine (6-OHDA) treatment was combined with data mining and clustering techniques to identify distinct functional subgroups of cell stress genes (Holtz et al., Antioxidants & Redox Signaling. 2005; 7: 639-648). 6-OHDA is a parkinsonian mimetic has been shown to cause transcriptional changes associated with cellular stress and the UPR.

Apoptosis. In addition, as stated above, prolonged, persistent ER stress that is not eliminated by the UPR can also lead to programmed cell death in neuronal cells, e.g., apoptosis. For in vitro evaluation, neuronal cell lines such as hNT2 (ATCC accession # CRL-10742), Hs68 (# CRL-1636), HCN-1A (# CRL-10442), SK-N-FI (# CRL-2142), SK-N-DZ (# CRL-2149), SK-N-SH (# HTB-11), or NT2/D1 (# CRL-1973), or embryonic stem cells or neural stem cells that have been differentiated in vitro to neurons (see, e.g., US 2003/0013192 to Laeng et al.; and Yan et al., Stem Cells. 2005; 23:781-90), can be transfected with mutant Gba and evaluated for apoptosis.

Thus, the number of apoptotic cells can be measured using fluorescent substrate analogs for, e.g., caspase 3, an early indicator of apoptosis. Apoptosis can be detected using numerous methods in the art, including fluorescent activated cell sorting (FACS), and/or using a fluorescent plate reader (e.g., 96 wells for high-throughput). For the latter, the percentage of cells positive for apoptosis or cell death can be determined, or fluorescence intensity can be measured relative to the protein concentration.

Cell/organelle morphology. Morphological abnormalities in neurons can result from mutant protein accumulation and can be evaluated using morphometric analysis. For example, changes in neuron morphology in neurons transfected with tau-GFP included asymmetry, a reduction in the number of axons in the anterior and posterior projections, abnormal axon bundling, axon blebbing, and reduced terminal arborisations. Other alterations in cell morphology including aggregation, cell size (cell area or cell density), polymegathism (variation of cell size such as coefficient of variation of mean cell area), pleomorphism (variation of cell shape such as percent of hexagonal cells or coefficient of variation of cell shape), cell perimeter, average cell side length, cell shape, and so forth. Morphology can be evaluated using quantitative morphometric analysis according to methods described in, Ventimiglia et al., *J Neurosci Methods*. 1995; 57:63-6; and Wu et al., *Cerebral Cortex*. 2004; 14: 543-54 (high-throughput analysis); and using image analysis software such as Image Pro-Plus software Cell/ER stress can also be detected by evaluating organelle morphology. For example, the UPR in CY028-expressing *S. cerevisiae* cells was manifested as an aberrant morphology of the endoplasmic reticulum (ER) and as extensive membrane proliferation compared to the ER morphology and membrane proliferation of wild-type CY000-producing *S. cerevisiae* cells (Sagt et al., *Applied and Environmental Microbiology*. 2002; 68: 2155-2160).

Moreover, specific morphological indicators can be associated with individual aggregation diseases. For example, in Gaucher disease, the lipids accumulate in lysosomes of macrophages resulting in a distinct morphology indicative of an activated macrophage.

ER calcium stores. ER stress also can be detected by measuring the levels of calcium in the ER lumen and cytosol, and also by determining the level of calcium regulatory proteins such as SERCA2b, a ubiquitous calcium-ATPase which regulates intracellular calcium stores. As a control, ER stress can be induced by calcium depletion, using, e.g., thapsigargin.

Proteasome function. Proteasome function, one cell stress response to accumulation of proteins or substrates, can be measured according to the method of Glas et al. (*Nature*. 1998; 392: 618-622). Evaluation of 26S proteasome function in living animals by imaging has been achieved ubiquitin-luciferase reporter for bioluminescence imaging (Luker et al., *Nature Medicine*. 2003. 9, 969-973). Proteasome isolation and assays are described in Craiu et al., JBC. Kits for proteasome isolation are commercially available from, for example, Calbiochem (Cat. No. 539176). This kit can be used to isolate proteasome subunits from cell extracts to study their function and interactions with other proteins. The proteasome subunits can be identified by loading the beads directly onto an SDS-PAGE gel and immunoblotting with subunit specific antibodies. Alternatively, proteasome bound to the beads can be used in proteolytic assays using proteasome substrates.

pH cell growth and trafficking assays. Trafficking of proteins in cells occurs along pH gradients (i.e., ER pH about 7.0, Golgi pH about 6.2-7.0, trans-Golgi network pH about 6.0, early and late endosomes pH about 6.5, lysosomes pH about 4.5). Trafficking, lysosome/endosome morphologies, and luminal pHs are also disrupted in some lysosomal storage diseases (Ivleva et al., *Biomed Sci*. 1991; 2: 398-402; Futerman and van Meer, *Nat Rev Mol Cell Biol*. 2004; 5: 554-65), and elevated pH in the endosome has been shown to promote a reversal of vesicular trafficking from endosomes to Golgi (van Wert et al., 1995, supra).

The growth rate of cells (e.g., wild-type, untreated patient cells and chaperone treated patient cells) exposed to a range of pHs can be measured and compared using a fluorescent plate reader. Apoptosis and cell death assays (described above) can also be used to determine pH-sensitivity on cell viability.

Alternatively, lysosomal pH and pH effects on trafficking can be evaluated using a confocal microscope. pH-sensitive fluorescent probes that are endocytosed by the cells can be used to measure pH ranges in the lysosomes and endosomes (i.e., fluorescein is red at pH 5.0 and blue to green at pH 5.5 to 6.5). *Lysosome* morphology and pH can be compared in wild type and chaperone treated and untreated patient cells. This assay can be run in parallel with the plate reader assay to determine the pH-sensitivity. In addition, trafficking of enzymes to the lysosome can be evaluated in cells at different pH's using the dual labeling experiments described above.

Rates of endocytosis for cells (wild type, chaperone treated and untreated patient cells) exposed to various pHs can be measured using Quantum dots or Dextran Blue. In addition, assays describing the use of fluorescent lipid analogs (BODIPY-LacCer, -GM1 gangliosides etc.) are described in Pagano, *Phil Trans R Soc Lond B*. 2003; 358-885-91.

Enzyme activity. In addition to evaluating the effect of chaperones on aggregation and/or trafficking, using the protein localization assays described above, biochemical assays can also be used to determine whether the proteins are functional, and to assess the effects of restoring function, once they have been chaperoned out of the ER, e.g., to the lysosome. Activity assays are generally designed to measure the activity of a target protein in the presence or absence of a test agent. Such assays will depend on the specific protein. For example, where the protein is an enzyme, intracellular enzyme activity assays using substrates are routine in the art can be used to assess enzyme activity.

Ex vivo and in vivo evaluation of enzyme activity can be performed using normal animals and animal models of disease states such as described infra.

Methods of Diagnosis

The present invention provides a method for diagnosing a risk factor, condition, or neurological disorder associated with a mutation in a lysosomal enzyme. Since neurological effects which occur in patients with LSDs can be present in other neurological disorders, persons with mutations in the lysosomal enzymes, but who have not been diagnosed with an LSD may not be effectively treated. One example is individuals with heterozygous mutations in the Gba gene, who are at risk of developing, or have developed parkinsonism or Parkinson's disease. Other exemplary neurological symptoms that may be associated with a mutant lysosomal enzyme include neurodegeneration, neurological regression, seizures, blindness, eye movement disorders, spacisticity, dementia; developmental delays; neuromuscular symptoms, peripheral neuropathy (neuropathic pain), acroparesthesia, impairments in long-term memory, cerebrovascular events such as cerebrovascular events (stroke, transient ischemic attack), and impaired swallowing.

Methods of identifying a mutation or mutations in lysosomal enzymes are well-known in the art and include comparing enzyme activity of a lysosomal enzyme from a biological sample from an individual exhibiting neurological symptoms, or an individual who is at risk of developing neurological symptoms (such as a carrier for an LSD or a relative of an individual having a LSD. Methods of identifying mutations at a molecular level, i.e., nucleotide or amino acid alterations, also are well known to those skilled in the art, such as PCR amplification followed by sequencing, single strand conformation polymorphism (SSCP) or using DNA microarrays for large samples (Tennis et al., *Cancer Epidemiology Biomarkers & Preventio*. 2006; 15: 80-85)

Formulation, Dosage, and Administration of Specific Pharmacological Chaperones

The present invention provides that the specific pharmacological chaperone be administered in a dosage form that permits systemic administration, since the compounds need to cross the blood-brain barrier to exert effects on neuronal cells. In one embodiment, the specific pharmacological chaperone is administered as monotherapy, preferably in an oral dosage form (described further below), although other dosage forms are contemplated. In one embodiment, it is contemplated that the dosing regimen should be one that provides a periodic peak level of compound in the plasma of the individual being treated. Other embodiment may require constant, steady state levels of compound in plasma. This can be obtained either by daily administration in divided doses, or controlled-release formulations, or by less frequent administration of sustained-release dosage forms. Formulations, dosage, and routes of administration for the specific pharmacological chaperone are detailed below.

Formulations

The specific pharmacological chaperone can be administered in a form suitable for any route of administration, including e.g., orally in the form tablets or capsules or liquid, or in sterile aqueous solution for injection. When the specific pharmacological chaperone is formulated for oral administration, the tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled or sustained release of the specific pharmacological chaperone.

The pharmaceutical formulations of the specific pharmacological chaperone suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alchohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the specific pharmacological chaperone in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The formulation can also contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

Administration

The route of administration of the specific pharmacological chaperone may be oral (preferably) or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations of the specific pharmacological chaperone may be by periodic injections of a bolus of the preparation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

Dosage

The amount of specific pharmacological chaperone effective to rescue the endogenous mutant Gba can be determined on a case-by-case basis by those skilled in the art. Pharmacokinetics and pharmacodynamics such as half-life ($t_{1/2}$), peak plasma concentration ($C_{max}$), time to peak plasma concentration ($t_{max}$), exposure as measured by area under the curve (AUC), and tissue distribution for both the replacement protein and the specific pharmacological chaperone, as well as data for specific pharmacological chaperone/Gba binding (affinity constants, association and dissociation constants, and valency), can be obtained using ordinary methods known in the art to determine compatible amounts required to stabilize the replacement protein, without inhibiting its activity, and thus confer a therapeutic effect.

Data obtained from cell culture assay or animal studies may be used to formulate a therapeutic dosage range for use in humans and non-human animals. The dosage of compounds used in therapeutic methods of the present invention preferably lie within a range of circulating concentrations that includes the $ED_{50}$ concentration (effective for 50% of the tested population) but with little or no toxicity. The particular dosage used in any treatment may vary within this range, depending upon factors such as the particular dosage form employed, the route of administration utilized, the conditions of the individual (e.g., patient), and so forth.

A therapeutically effective dose may be initially estimated from cell culture assays and formulated in animal models to achieve a circulating concentration range that includes the $IC_{50}$. The $IC_{50}$ concentration of a compound is the concentration that achieves a half-maximal inhibition of symptoms (e.g., as determined from the cell culture assays). Appropriate dosages for use in a particular individual, for example in human patients, may then be more accurately determined using such information.

Measures of compounds in plasma may be routinely measured in an individual such as a patient by techniques such as high performance liquid chromatography (HPLC) or gas chromatography.

Toxicity and therapeutic efficacy of the composition can be determined by standard pharmaceutical procedures, for example in cell culture assays or using experimental animals to determine the $LD_{50}$ and the $ED_{50}$. The parameters $LD_{50}$ and $ED_{50}$ are well known in the art, and refer to the doses of a compound that is lethal to 50% of a population and therapeutically effective in 50% of a population, respectively. The dose ratio between toxic and therapeutic effects is referred to as the therapeutic index and may be expressed as the ratio: $LD_{50}/ED_{50}$. Specific pharmacological chaperones that exhibit large therapeutic indices are preferred.

The optimal concentrations of the specific pharmacological chaperone are determined according to the amount required to stabilize and induce a proper conformation of the recombinant protein, e.g., Gba, in vivo, in tissue or circulation, without persistently preventing its activity, bioavailability of the specific pharmacological chaperone in tissue or in circulation, and metabolism of the specific pharmacological chaperone in tissue or in circulation. For example, where the specific pharmacological chaperone is an enzyme inhibitor, the concentration of the inhibitor can be determined by calculating the $IC_{50}$ value of the specific chaperone for the enzyme. Taking into consideration bioavailability and metabolism of the compound, concentrations around the $IC_{50}$ value or slightly over the $IC_{50}$ value can then be evaluated based on effects on enzyme activity, e.g., the amount of inhibitor needed to increase the amount of enzyme activity or prolong enzyme activity of the administered enzyme. As an example, the $IC_{50}$ value of the compound isofagomine for the Gba enzyme is 0.04 µM, indicating that it is a potent inhibitor.

Combination Drug Therapy

The specific pharmacological chaperone can be used to treat patients with CNS disorders that are associated with mutations in lysosomal enzymes in combination with other drugs that are also used to treat the CNS disorder.

For example, for patients having Parkinson's disease, such as dopamine receptor agonists, anticholinergics, COMT inhibitors, monoamine oxidase B inhibitors. Exemplary agents include but are not limited to levodopa (Sinemet®; Merck), Parlodel® (bromocriptine mesylate; Novartis); Permax® (pergolide mesylate; Eli Lilly); Requip® (ropinirole HCl), Mirapex® (pramipexole dihydrochloride); Cogetin® (benztropine mesylate); Artane® (trihexyphenidyl HCl; American Cyanamid); Symmetrel® (amantadine hydrochloride; Du Pont Merck); and Eldepryl® (Somerset Pharmaceuticals).

Combination Therapy with Gene Therapy

Although not yet approved for therapeutic treatment in the United States, gene therapies (both ex vivo and direct transfer) for numerous genetic disorders are under investigation. The present invention also contemplates use of the specific pharmacological chaperone in combination with gene therapy to replace the defective Gba gene in the neurological disease. Such a combination will enhance the efficacy of gene therapy by increasing the level of expression of the therapeutic Gba in vivo, since, in addition to enhancing folding and processing of mutated enzymes, specific pharmacological chaperones have been shown to enhance folding and processing of the wild-type or conformationally stable counterparts (see, e.g., U.S. Pat. No. 6,274,597 to Fan et al., Example 3).

U.S. Pat. No. 6,309,634 to Bankiewicz describes a gene therapy approach for treating Parkinson's disease. According to the method, recombinant adeno-associated virus (rAAV) virions are produced in vitro and comprise a nucleic acid sequence encoding aromatic amino acid decarboxylase (AADC). Another group recently inserted the gene for glial cell line-derived neurotrophic factor (GDNF), also via recombinant adeno-associated viral vectors, in a monkey model of Parkinson's disease (Eslamboli et al., *J Neurosci.* 2005; 25(4):769-77).

Any of the methods for gene therapy which are or become available in the art can be used to deliver therapeutic genes. Exemplary methods are described below. For general reviews of the methods of gene therapy, see Goldspiel et al., Clinical Pharmacy 1993, 12:488-505; Wu and Wu, Biotherapy 1991, 3:87-95; Tolstoshev, *Ann. Rev. Pharmacol. Toxicol.* 1993, 32:573-596; Mulligan, *Science.* 1993, 260:926-932; and Morgan and Anderson, *Ann. Rev. Biochem.* 1993, 62:191-217; May, *TIBTECH* 1993, 11:155-215. Methods commonly known in the art of recombinant DNA technology that can be used are described in Ausubel et al., (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al., (eds.), 1994, *Current Protocols in Human Genetics*, John Wiley & Sons, NY; and Colosimo et al., *Biotechniques* 2000; 29(2):314-8, 320-2, 324.

The gene to be administered for the methods of the present invention can be isolated and purified using ordinary molecular biology, microbiology, and recombinant DNA techniques within the skill of the art. For example, nucleic acids encoding the target protein can be isolated using recombinant DNA expression as described in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y.; *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Ê Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Ê Perbal, *A Practical Guide To Molecular Cloning* (1984). The nucleic acid encoding the protein may be full-length or truncated, so long as the gene encodes a biologically active protein.

The identified and isolated Gba gene can then be inserted into an appropriate cloning vector. Vectors suitable for gene therapy include viruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression.

In a specific embodiment, the vector is a viral vector. Viral vectors, especially adenoviral vectors can be complexed with a cationic amphiphile, such as a cationic lipid, polyL-lysine (PLL), and diethylaminoethyldextran (DELAE-dextran), which provide increased efficiency of viral infection of target cells (See, e.g., PCT/US97/21496 filed Nov. 20, 1997, incorporated herein by reference). Viral vectors for use in the present invention include vectors derived from vaccinia, herpesvirus, AAV and retroviruses. In particular, herpesviruses, especially herpes simplex virus (HSV), such as those disclosed in U.S. Pat. No. 5,672,344, the disclosure of which is incorporated herein by reference, are particularly useful for delivery of a transgene to a neuronal cell. AAV vectors, such as those disclosed in U.S. Pat. Nos. 5,139,941, 5,252,479 and 5,753,500 and PCT publication WO 97/09441, the disclosures of which are incorporated herein, are also useful since these vectors integrate into host chromosomes, with a minimal need for repeat administration of vector. For a review of viral vectors in gene therapy, see McConnell et al., *Hum Gene Ther.* 2004; 15(11):1022-33; Mccarty et al., *Annu Rev Genet.* 2004; 38:819-45; Mah et al., *Clin. Pharmacokinet.* 2002; 41(12):901-11; Scott et al., *Neuromuscul. Disord.* 2002; 12 Suppl 1:S23-9. In addition, see U.S. Pat. No. 5,670,488.

The coding sequences of the gene to be delivered are operably linked to expression control sequences, e.g., a promoter that directs expression of the gene. As used herein, the phrase "operatively linked" refers to the functional relationship of a polynucleotide/gene with regulatory and effector sequences of nucleotides, such as promoters, enhancers, transcriptional and translational stop sites, and other signal sequences. For example, operative linkage of a nucleic acid to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

In one specific embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, *Proc. Natl. Acad. Sci. USA*. 1989, 86:8932-8935; Zijlstra et al., *Nature*. 1989, 342: 435-438; U.S. Pat. No. 6,244,113 to Zarling et al.; and U.S. Pat. No. 6,200,812 to Pati et al.).

Gene Delivery

Delivery of the vector into a patient may be either direct, in which case the patient is directly exposed to the vector or a delivery complex, or indirect, in which case, cells are first transformed with the vector in vitro, then transplanted into the patient. These two approaches are known, respectively, as in vivo and ex vivo gene therapy.

Direct transfer. In a specific embodiment, the vector is directly administered in vivo, where it enters the cells of the organism and mediates expression of the gene. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-β-1-64-N-acetylglucosamine polysaccharide; see U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, *J. Biol. Chem.* 1987, 62:4429-4432), etc. In another embodiment, a nucleic acid-ligand complex can be formed in which the ligand comprises a fusogenic viral peptide to disrupt endosomes, allowing the nucleic acid to avoid lysosomal degradation, or cationic 12-mer peptides, e.g., derived from antennapedia, that can be used to transfer therapeutic DNA into cells (Mi et al., *Mol. Therapy*. 2000, 2:339-47). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188). Recently, a technique referred to as magnetofection has been used to deliver vectors to mammals. This technique associates the vectors with superparamagnetic nanoparticles for delivery under the influence of magnetic fields. This application reduces the delivery time and enhances vector efficacy (Scherer et al., *Gene Therapy*. 2002; 9:102-9). Additional targeting and delivery methodologies are contemplated in the description of the vectors, below.

In a specific embodiment, the nucleic acid can be administered using a lipid carrier. Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, *Nature*. 1989; 337:387). Intravenous injection of cationic lipid-plasmid complexes into mice has been shown to result in expression of the DNA in lung (Brigham et al., *Am. J. Med. Sci.* 1989; 298:278). See also, Osaka et al., *J. Pharm. Sci.* 1996; 85(6):612-618; San et al., *Human Gene Therapy*. 1993; 4:781-788; Senior et al., *Biochemica et Biophysica Acta*. 1991; 1070:173-179); Kabanov and Kabanov, *Bioconjugate Chem*. 1995; 6:7-20; Liu et al., *Pharmaceut. Res.* 1996; 13; Remy et al., *Bioconjugate Chem.* 1994; 5:647-654; Behr, J-P., *Bioconjugate Chem.* 1994; 5:382-389; Wyman et al., *Biochem*. 1997; 36:3008-3017; U.S. Pat. No. 5,939,401 to Marshall et al; and U.S. Pat. No. 6,331,524 to Scheule et al.

Representative cationic lipids include those disclosed, for example, in U.S. Pat. No. 5,283,185; and e.g., U.S. Pat. No. 5,767,099, the disclosures of which are incorporated herein by reference. In a preferred embodiment, the cationic lipid is N4-spermine cholesteryl carbamate (GL-67) disclosed in U.S. Pat. No. 5,767,099. Additional preferred lipids include N4-spermidine cholestryl carbamate (GL-53) and 1-(N4-spermine)-2,3-dilaurylglycerol carbamate (GL-89).

Preferably, for in vivo administration of viral vectors, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors. In that regard, it is advantageous to employ a viral vector that is engineered to express a minimal number of antigens.

Indirect transfer. Somatic cells may be engineered ex vivo with a construct encoding a wild-type protein using any of the methods described above, and re-implanted into an individual. This method is described generally in WO 93/09222 to Selden et al. In addition, this technology is used in Cell Based Delivery's proprietary ImPACT technology, described in Payumo et al., *Clin. Orthopaed. and Related Res.* 2002; 403S: S228-S242. In such a gene therapy system, somatic cells (e.g., fibroblasts, hepatocytes, or endothelial cells) are removed from the patient, cultured in vitro, transfected with the gene(s) of therapeutic interest, characterized, and reintroduced into the patient. Both primary cells (derived from an individual or tissue and engineered prior to passaging), and secondary cells (passaged in vitro prior to introduction in vivo) can be used, as well as immortalized cell lines known in the art. Somatic cells useful for the methods of the present invention include but are not limited to somatic cells, such as fibroblasts; keratinocytes, epithelial cells, endothelial cells, glial cells, neural cells, formed elements of the blood, muscle cells, other somatic cells that can be cultured, and somatic cell precursors. In a preferred embodiment, the cells are fibroblasts or mesenchymal stem cells.

Nucleic acid constructs, which include the exogenous gene and, optionally, nucleic acids encoding a selectable marker, along with additional sequences necessary for expression of the exogenous gene in recipient primary or secondary cells, are used to transfect primary or secondary cells in which the encoded product is to be produced. Such constructs include but are not limited to infectious vectors, such as retroviral, herpes, adenovirus, adenovirus-associated, mumps and poliovirus vectors, can be used for this purpose.

Mesenchymal stem cells (MSCs) are non-blood-producing stem cells produced in the bone marrow. MSCs can be made to differentiate and proliferate into specialized non-blood tissues. Stem cells transfected with retroviruses are good candidates for the therapy due to their capacity for self-renewal. This ability precludes repetitive administration of the gene therapy. Another advantage is that if the injected stem cells reach the target organ and then differentiate, they can replace the damaged or malformed cells at the organ.

As one example, for Gaucher disease, trials are underway for transduction of somatic stem cells from an individual with a retrovirus encoding the Gba gene, followed by returning the corrected stem cells to the patient, where they take up residence in the bone marrow and produce Gba-expressing cells such as macrophages.

Chaperone Delivery. When administered in combination with gene therapy encoding a therapeutic gene, the specific pharmacological chaperone can be administered according to the methods and dosage forms described above.

Combination with Substrate Inhibitors

In addition, combination of small molecule chaperones of this invention with other small molecule substrate inhibitors, as described in the background, is also contemplated. Since even a slight reduction in lysosomal enzyme activity can lead to elevated lipid accumulation, which can, in turn, alter the phospholipid balance of the cell or initiate signaling events that result in apoptosis. Exemplary substrate inhibitors include NB-DNJ (Miglustat) for inhibition of ceramide specific glucosyltransferases (reduction of glycolipid substrates) (Kasperzyk et al., *Journal of Neurochemistry* 2004. 89: 645-653).

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Determination of Increased Gba Activity in the Brains of L444P Transgenic Mice Treated with Specific Pharmacological Chaperones L444P is a mutation associated with Types 2 and 3 Gaucher disease. L444P transgenic mice (homozygous for human L444P mutated Gba on a glucosylceramide synthase null background) exhibit a deficiency in Gba activity in the brain. However, due to the disruption in the glucosylceramide synthase gene, these mice do not exhibit accumulation of GluCer in e.g., macrophages. Concomitant glucosylceramide synthase disruption is necessary, since previously made L444P transgenic mice died within 3 days of birth due to impaired permeability barrier function in the epidermis.

In this experiment, the L444P transgenic mice were treated with isofagomine or C-benzyl-isofagomine and surrogate markers were measured at 1, 3, 6 and 12 months to determine efficacy of the chaperones. In addition, mice in a "washout" period of 2 weeks of non-chaperone treatment following 4 weeks of treatment were also evaluated for reversion of surrogate markers back to levels seen in untreated controls.

Methods

Specific pharmacological chaperone treatment. Mice were administered isofagomine or C-benzyl-isofagomine in their drinking water, ad libitum. Estimated daily dosage based on the volume of water consumed is about 10 mg/kg/day.

Gba activity assays in brain. At the end of 1, 3, 6 and 12 months, mice were sacrificed and evaluated for enhancement of Gba enzyme activity in brain. Brian tissue is freshly harvested (blood washed away with PBS), or thawed from frozen stock. Tissue is minced tissue and homogenized on ice in 200-500 µl McIlvaine (MI) buffer (0.25% sodium taurocholate, 0.1% Triton x-100 in 0.1M citrate and 0.2M phosphate buffer, pH 5.2), and centrifuged at 10,000×g. The supernatant is collected and may be frozen at this step.

About 1-10 µl of supernatant from the brain tissue homogenates is added to a clear 96-well plate for the Micro BCA Protein Assay (Pierce, cat# 23235) to quantitate the amount of total protein according to the manufacturer's protocol. As a negative control, another 10 µl is added to a black plate, mixed with 10 µl of 2.5 mM CBE (2.7 mg Conduritol B Epoxide in 6.7 ml buffer), an inhibitor of Gba activity, and left at room temperature (RT) for 30 minutes. 50 µl of 3 mM 4-methal Umbelliferal beta-D-glucoside (4-MU-beta-D-glucoside; made fresh, powder is dissolved in 0.2 ml of DMSO, then q.s. to proper volume with MI buffer), a Gba substrate, is then added, and the black plate is further incubated at 37° C. for 1 hr. After incubation, 10 µl of supernatant is added to a second black plate, mixed with 10 µl of MI buffer and 50 µl 6 mM of Gba substrate 4-MU-beta-D-glucoside, and incubated at 37° C. for 1 hr. The reaction is then stopped by adding 70 µl 0.2 M glycine, pH 10.8. The plate is read in a plate-reader (Victor2 1420 multilabel counter; Wallac) at $F_{460}$.

Relative beta-glucose activity is determined by the following equation:

$$F_{460} \text{ without CBE} - F_{460} \text{ with CBE}/(A_{550} \text{ sample} - A_{550} \text{ buffer})$$

$F_{460}$ reading is converted into nmole 4-MU based on 4-MU standard curve and $A_{550}$ is converted into mg of protein based on the protein standard curve. One unit of Gba activity is defined as nmole of 4-MU released in one hour.

Washout study. To determine if and in what time frame the effects of drinking water dosed AT2101 on L444P mice regress after cessation of the treatment, a washout study was performed. Nine male 3 month old L444P mice were dosed at about 10 mg/kg/day for 4 weeks with an equal number of mice untreated as a control. Four treated and four untreated mice were sacrificed at the end of 4 weeks, and the remaining animals were not further treated with isofagomine, i.e., they were given normal drinking water, for another two weeks prior to sacrifice and evaluation of the Gba activity in brain.

Results

Gba Activity in Brain. Significant increase in Gba activity was observed after as little as two weeks of treatment with isofagomine in brain (FIG. 1A), which persisted through 4-12 weeks. Notably, in brain, isofagomine treatment resulted in an increase from about 1 U/mg in untreated mice, to about 4.5 U/mg after 2 and 4 weeks of treatment, and further increased to about 6 U/mg after 12 weeks (p<0.001). It is expected that increased Gba activity will persist at 3, 6 and 12 months and for as long as the chaperones are administered.

Similarly, after two weeks, the C-benzyl-isofagomine-treated mice also exhibited significant increased Gba activity in the organs such as spleen, and a trend toward increased activity in the lung and brain (data not shown). It is expected that increases in Gba activity will be observed in other organs, including the brain, upon further treatment, since after two weeks of treatment with AT2206, there was a trend toward increase in the brain (data not shown).

Washout. Similar to above, after 4 weeks of treatment at 10 mg/kg/day, Gba activity was significantly elevated in brain in the L444P transgenic mice. (FIG. 1B).

Discussion

These results provide the first indication that physiological levels of chaperone are sufficient to cross the blood-brain barrier enhance activity of Gba in the brain and in the peripheral organs (e.g., spleen and liver). This is surprising since peripherally administered agents often have to be administered in higher doses to be effective in the brain. In the case where Gba inhibitors at below-inhibitory are used as chaperones, high doses of inhibitor in the periphery would be inhibitory for mutant Gba, thereby defeating the purpose of enhancing enzyme activity as previously demonstrated. Similar results were obtained in monkeys treated with IFG, where IFG was detected in the CSF following treatment.

Example 2

Restoration of Disrupted Lysosomal Trafficking in Gaucher Fibroblasts

Although N370S Gaucher fibroblasts (from a human patient) do not demonstrate an accumulation of substrate (i.e., GluCer) in the cytoplasm, these fibroblasts exhibit abnormal lysosomal protein and Gba staining compared with wild-type fibroblasts. Treatment of N370S fibroblasts with pharmacological chaperone isofagomine increased the amount of Gba seen in the lysosome and restored a normal lysosomal staining pattern to the cells.

Methods

Cell culture. N370S fibroblasts (DMN89.15) were cultured in DMEM with 10% FBS and 1% penn/strep at 37C with 5% $CO_2$. Wild-type fibroblast cell line CRL-2097 form a healthy individual was used as a control. Cells were subcultured from 10 cm plates into 12-well plates with cover slips. Cells from one confluent 10 cm plate were diluted in 38 ml of culture medium. Isofagomine or C-benzyl-isofagomine were added from a 10 mM stock solution (5% DMSO) to each well of a 12-well plate at the following concentrations:

C-benzyl-isofagomine-control (secondary antibody only); untreated; 0.03 µM; 0.1 µM; 0.3 µM; 1.0 µM; 3.0 µM; and 10.0 µM.

Isofagomine-control (secondary antibody only); untreated; 10 µM; 30 µM; 100 µM; 1 nM; 3 nM; and 10 nM.

Cells were cultured for a total of about 6 days.

Fixing and Staining. Cells were washed for 5 minutes in PBS, fixed for 15 minutes in 3.7% paraformaldahyde (in PBS), washed again for 5 minutes in PBS, and permeabilized with 0.5% saponin for 5 minutes. Cells were then washed with PBS containing 0.1% saponin, treated for 5 minutes with fresh 0.1% sodium borohydride/0.01% saponin, and washed 3 times with PBS with 0.1% saponin/1% BSA for 5 minutes each.

Cells were incubated for 1 h with 500 µl of primary anti-Gba (1:200) or anti-LAMP-1 (1:200; BD Pharmingen, Cat. No. 555798) antibody solution in PBS with 1% BSA. Lysosomal staining using LysoTracker® Red (Cambrex, East Rutherford, N.J.) was performed according to the manufacturer's instructions. Following incubation, cells were washed 3 times in 1% BSA containing 0.1% saponin in PBS, followed by incubation with the secondary antibody solution (1:500; anti-rabbit AlexaFluor588 for anti-Gba and anti-mouse IgG AlexaFluor594 for anti-LAMP-1). Cells were mounted onto coverslips, sealed, and immediately viewed.

Confocal Microscopy. Cells were visualized using a confocal microscope. The red and green channel gains were set to 6 and the laser power was optimized using the intensity window, and were not adjusted for the rest of the experiment. All slides were analyzed at the same sitting and all images were gathered without any zoom using the 20× and 60× lens, the small pinhole, optimal pixel size, an average of 2 scans, and red and green channels were acquired simultaneously as in all previous experiments.

All images were displayed at the same intensity and red+green channel intensity graphs were generated for each image by placing the cursor over the maximum number of cells.

Future measurements can be made by calculating a ratio for overlapping red (LAMP-1) and green (GBA) pixels.

Results

Figure 2:
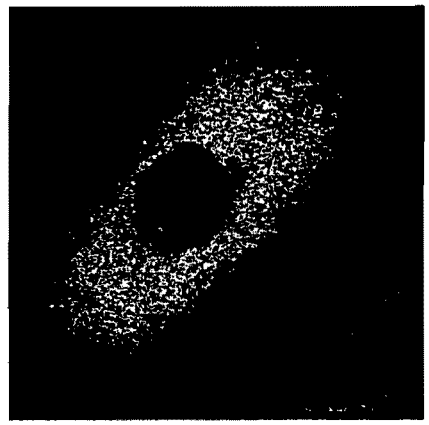
FIG. 2 depicts fluorescent staining of lysosomes using LysoTracker® Red in cells from Gaucher fibroblasts (2A) and normal fibroblasts (2B). Staining for lysosomal protein LAMP-1 was also performed on normal fibroblasts (2C) and Gaucher fibroblasts (2D).
Figure 2:
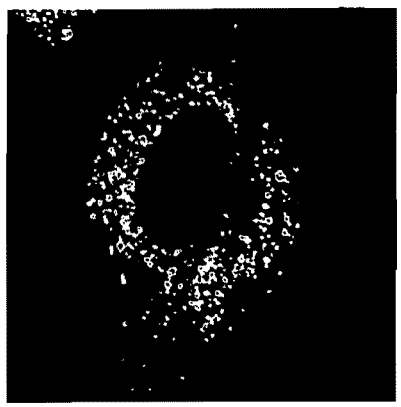
Figure 2:
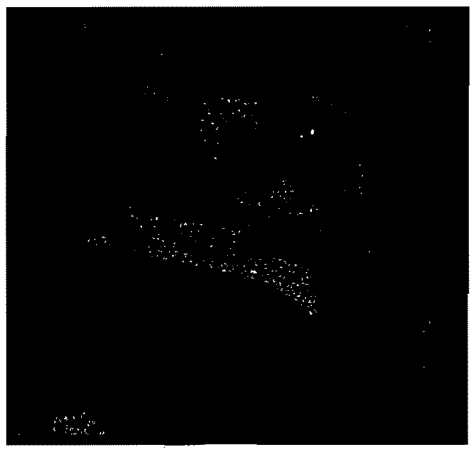
Figure 2:
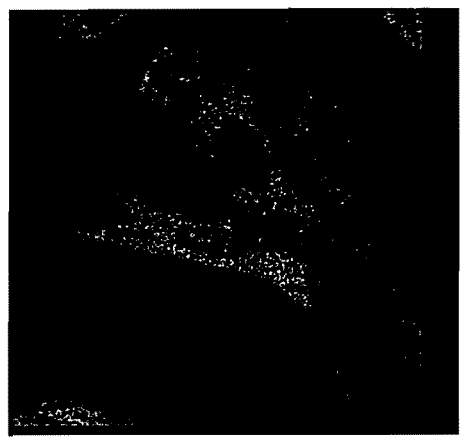
Figure 2:
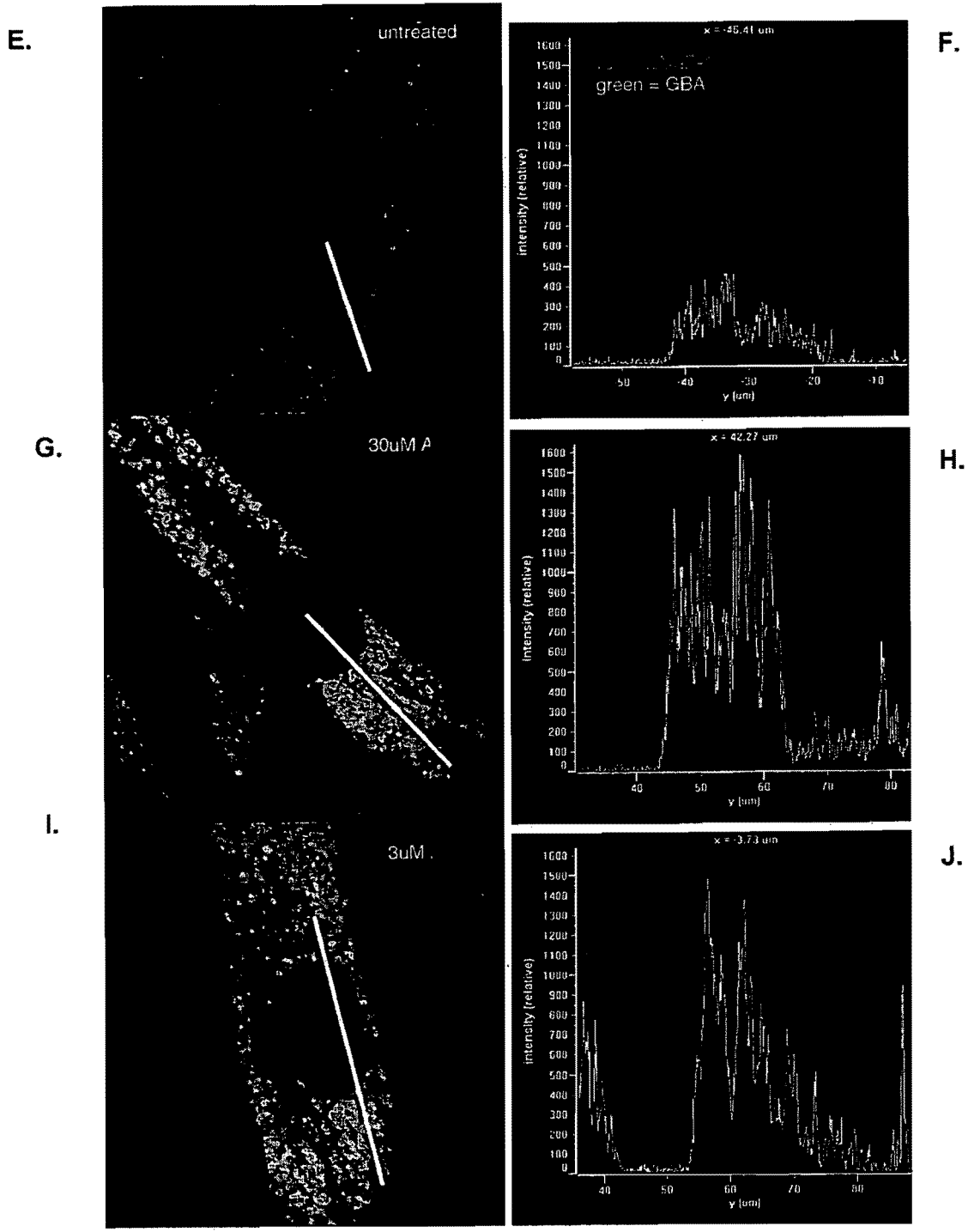
Figure 2:
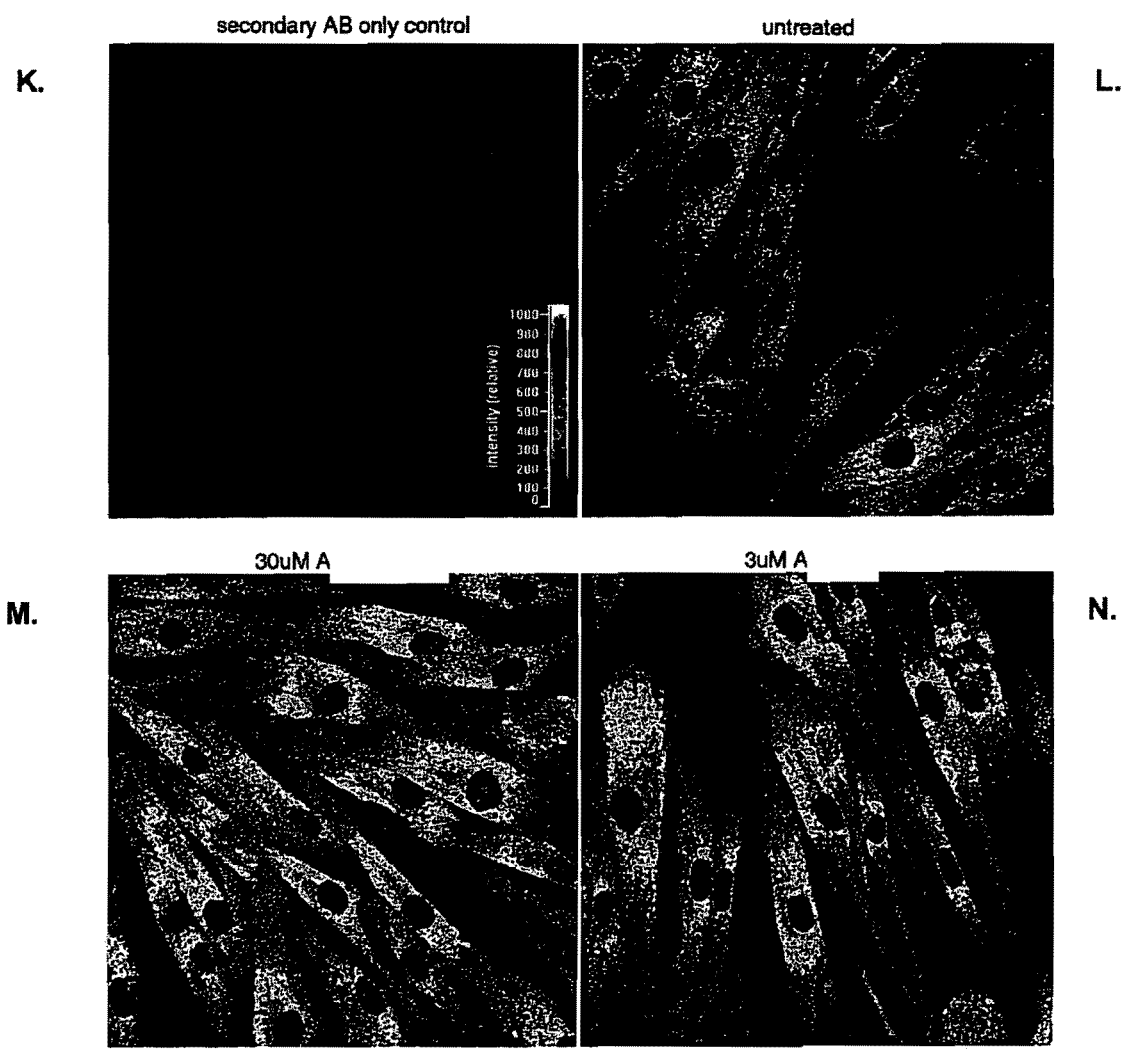

Gaucher N370S fibroblasts that have been confluent for more than 5 days exhibit a granular lysosmal staining pattern using LysoTracker® Red (FIG. 2A) compared with a normal fibroblast, which has a punctuate staining pattern (FIG. 2B). Similar results were shown for L444P fibroblasts (data not shown). Staining for lysosomal LAMP-1 is shown in both N370S and normal fibroblasts (FIGS. 2C-D, respectively). More LAMP-1 is shown in Gaucher fibroblasts.

Treatment with 30.0 µM isofagomine (AT2201) (FIGS. 2G-H) and 3.0 µl C-benzyl-isofagomine (AT2206) (FIG. 2I-J) increased the amount of Gba in the lysosomes and re-established a normal lysosome punctuate staining pattern for Gba and LAMP-1 compared with an untreated control (FIG. 2E-F), as indicated by dual staining.

FIGS. 2K-N shows changes in Gba lysosomal staining in N370S Gaucher fibroblasts as follows: (K)-control (secondary antibody only); (L)-untreated N370S fibroblasts; (M)-30 µM isofagomine; and (N) 3 µM C-benzyl-isofagomine. Gba staining is shown to localize to lysosomes in chaperone-treated versus untreated controls. Similar results were obtained for L444P Gaucher fibroblasts (data not shown).

This improvement in normal cell morphology with chaperone treatment is due to a decrease in the amount or accumulation of mutant Gba, possibly in the form of aggregates, in the ER and/or cytosol. Accordingly, this strategy could relieve CNS symptoms in Parkinson's patients with heterozygous N370S mutations, or heterozygous Gaucher patients with homozygous N370S mutations and parkinsonism/dementia.

Example 3

Increase of Polyubiquinated Proteins with Chaperone Treatment in Gaucher Fibroblasts; Restoration of the Proteasome Degradation Pathway Anti-polyubiquitinated protein (PUP) and anti-Gba labeling of healthy human fibroblast was compared with that in fibroblasts from a Gaucher patient having the L444P Gba mutation, and Gaucher patient fibroblasts having the N370S Gba mutation.

Methods

Cell culture. L444P Gaucher fibroblasts (cell line GM10915); N370S Gaucher fibroblasts (cell line DMN89.15); and fibroblasts from a healthy individual (CRL-2097) were cultured in DMEM with 10% FBS and 1% PS at 37C with 5% $CO_2$. Cells are sub-cultured from 10 cm plates into 12-well plates with sterile cover slips. N370S cells from one confluent T-75 flask were diluted 1:6 and cultured for another 4 days.

Chaperones isofagomine or C-benzyl-isofagomine are added from a 10 mM stock solution (5% DMSO) to each row of a 12-well plate at the following concentrations:

C-benzyl-isofagomine—untreated; control (secondary antibody only); 0.03 µM; 0.1 µM; 0.3 µM; 1.0 µM; 3.0 µM; and 10.0 µM.

Isofagomine—untreated; control (secondary antibody only); 10 µM; 30 µM; 100 µM; 1 nM; 3 nM; and 10 nM.

Fixing and staining. Cells are washed once in PBS for 5 minutes, followed by fixation for 15 minutes in fresh 3.7% paraformaldehyde. Cells were then washed once in PBS for 5 minutes, followed by permeabilization for 5 minutes in 0.2% Triton X-100. Cells were then washed again in PBS for 5 minutes and treated for 5-10 minutes with fresh 0.1% sodium borohydride. Cells were washed three times in PBS with 1% BSA (5 min each) prior to staining.

Cells are incubated for 1 hour with 500 µl of the following primary antibodies (diluted 1:200 in PBS with 1% BSA):
1. Mouse monoclonal antibody to ubiquitinated proteins clone FK1 (Affiniti Research Products Cat. No. Pw 8805)
2. Rabbit anti-Gba antibodies are commercially available, e.g., 8E4.

Cells were then washed three times with PBS with 1% BSA, followed by incubation for 1 hour with a 1:500 dilution of the following secondary antibodies:
1. Goat Anti-Mouse IgM (µ chain) AlexaFluor568 (Molecular Probes Cat. No. A21043);
2. Goat Anti-Rabbit IgG (H+L) highly cross absorbed AlexaFluor488 (Molecular Probes Cat. No. A11034)

Cells were washed three times in PBS with BSA, mounted, and stored at 4° C. prior to visualization.

Results

Figure 3:
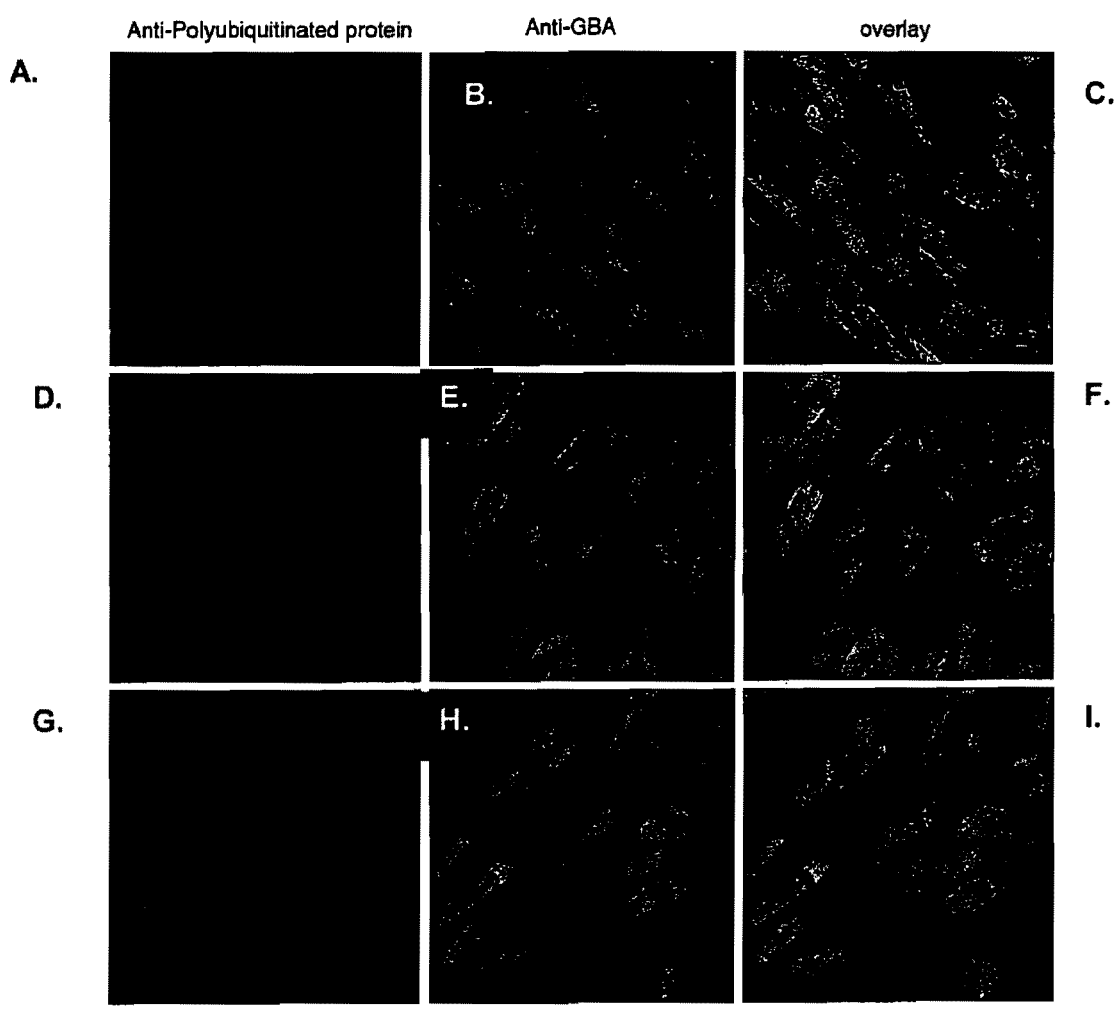
FIG. 3 depicts fluorescent staining of Gaucher cells (3D-I) and normal fibroblasts (3A-C) for the presence of polyubiquinated proteins (PUP) (3A, 3D, 3G) and Gba (3B, 3E, 3H), and an overlay for both (3C, 3F, 3I).

Initial experiments indicated that the concentration of polyubiquitinated proteins (PUP) in cells is greater (very intense) in healthy cells (FIGS. 3A and 3C) than in Gaucher N370S (FIGS. 3D and 3F) and L444P fibroblasts (FIGS. 3G and 3I) where staining is much less intense). Protein aggregation is known to inhibit the ubiquitin/proteasome pathway. Accordingly, decreasing aggregation using chaperones has a positive effect on the proteasome-mediated degradation pathway.

Discussion

Gaucher patients with the L444P mutation have extensive CNS involvement. This may be due to the fact that the human L444P mutant enzyme is known to be much more unstable than, e.g., the N370S mutant, making it even more likely that protein aggregates will form, and thereby inhibiting the ubiquitin/proteasome pathway (Tsuji et al., *N. Eng. J. Med.* 1987; 315: 570). Many other neurodegenerative diseases are caused by mutations which result in the accumulation of ubiquitinated proteins, and it has been further reported that protein aggregates may directly impair the ubiquitin/proteasome pathway and induce the expression of inflammatory mediators (Li et al., *The International Journal of Biochemistry & Cell Biology.* 2003; 35: 547-552).

If mouse L444P is stabilized using a specific pharmacological chaperone, the stress on the ubiquitin/proteasome pathway is alleviated by the increased Gba trafficking to the lysosome, thereby elongating the half-life of the mutant Gba-instead of being degraded in the ER it would traffic to the lysosome. This explains the increased PUP staining in normal fibroblasts compared to Gaucher fibroblasts.

Other Gba mutations that clinically do not result in overt CNS symptoms (i.e., N370S) may still result in the accumulation of the mutant protein in the ER and cytosol, causing additional stress on the ubiquitin/proteasome pathway or disrupting trafficking in neurons by decreasing the cells' ability to monoubiquitinate proteins.

\* \* \*

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A method for treating Parkinson's disease or parkinsonism in an individual, which method comprises administering to the individual an effective amount of (5R, 6R, 7S, 8S)-5-hydroxymethyl-2-octyl-5,6,7,8-tetrahydroimidazo[1,2-a]pyridine-6,7,8-triol.

2. The method of claim 1, wherein Parkinson's disease is early-onset Parkinson's disease.

3. The method of claim 1, wherein the individual is heterozygous or homozygous for a N370S mutation in a gene encoding glucocerebrosidase.

4. The method of claim 1, wherein the individual is heterozygous for a R496H mutation in a gene encoding glucocerebrosidase.

5. The method of claim 1, wherein the individual is heterozygous or homozygous for a L444P mutation in a gene encoding glucocerebrosidase.

6. The method of claim 1, wherein the individual has a mutation in a gene encoding β-glucocerebrosidase.

7. The method of claim 1, wherein the individual is heterozygous for an 84GG mutation.

* * * * *

UNITED STATES PATENT AND TRADEMARK OFFICE
CERTIFICATE OF CORRECTION

PATENT NO. : 8,883,813 B2  Page 1 of 1
APPLICATION NO. : 12/986506
DATED : November 11, 2014
INVENTOR(S) : Brandon Wutsman It is certified that error appears in the above-identified patent and that said Letters Patent is hereby corrected as shown below:

In the title page at (73) Assignee: "Amacus Therapeutics, Inc., Cranbury, NJ (US)" should be changed to --Amicus Therapeutics, Inc., Cranbury, NJ (US)--.

Signed and Sealed this
Twenty-ninth Day of March, 2016

Michelle K. Lee
*Director of the United States Patent and Trademark Office*

```
SEQUENCE LISTING

<160> NUMBER OF SEQ ID NOS: 4

<210> SEQ ID NO 1
<211> LENGTH: 8850
<212> TYPE: DNA
<213> ORGANISM: Homo sapiens

<400> SEQUENCE: 1
```

-continued

| | |
|---|---|
| tctagaaaga cttcactgag atcatttaaa gaacaaaaag gatggctggg gtccagcgca | 60 |
| gtggctcatg cctgtaatcc cagcactttc ggataccaag gcagcagatc acctgaggtc | 120 |
| cagagtttca gaccagcctg gccaacatag tgaaacccca tctctactaa aaataaaaaa | 180 |
| attagctgag catgttggag gcacctgta atcccagcta cttgggaggc tgaggcagga | 240 |
| gaatcactcg aacccaggag gtggaggttg cagtgagcca agatcacgcc actgcactcc | 300 |
| agcctgggca acagagtgag actctgtctc aaaaaacaac aacaacaaaa aatacaaaca | 360 |
| agagacaagt agttcccagg tgcctaccaa gtggtcaggc actgcactta cctcactgac | 420 |
| tgcagtaacc acccttgag gttgtggcat tgcctccatt ttccaggcaa ggaaatgggc | 480 |
| tgagagctgg gattagtcag gtcatgactg tgtgtgccac tcccgctaaa tctcatttga | 540 |
| tgtggttcat gaggccacac catggacagc ttcctccttg tgtccactga ggatatggct | 600 |
| ttgtacaaca ctttggtttt ttgaacgact ttacaaacct ccctgtcttg tgaggaagga | 660 |
| agaacagtta ttaccatctg catctgatga tgaaacaagg gacgctgcag aggagccgca | 720 |
| ctgaccactc cctccctcca gtcctgtcat cccactgcca gtgtcccacc ctcttgtgcc | 780 |
| ctgcacttca ctggctaata acccccctca cttttcctc tgtgaagcca tcctggataa | 840 |
| ttccccaccc acgaatggtc cctcctcatc tcagagagct ctccatgcac acctgttacc | 900 |
| gtttctgtct ttatctgtaa atatctgtgt gtctgacttc catgcctcac acacctctat | 960 |
| agggcaaaga ctgtcttaaa catcttggta gtgtcagtat tttgcacagt gaagttttt | 1020 |
| ttttttaaatt atatcagctt tatttgtacc tttttgacat ttctatcaaa aagaagtgt | 1080 |
| gcctgctgtg gttcccatcc tctgggattt aggagcctct accccattct ccatgcaaat | 1140 |
| ctgtgttcta ggctcttcct aaagttgtca cccatacatg ccctccagag ttttataggg | 1200 |
| catataatcg taacagatga gaggaagcca attgcccttt agaaatatgg ctgtgattgc | 1260 |
| ctcacttcct gtgtcatgtg acgctcctag tcatcacatg acccatccac atcgggaagc | 1320 |
| cggaattact tgcagggcta acctagtgcc tatagctaag gcaggtacct gcatccttgt | 1380 |
| ttttgtttag tggatcctct atccttcaga gactctggaa cccctgtggt cttctcttca | 1440 |
| tctaatgacc ctgaggggat ggagttttca agtccttcca gagaggtaag agagagagct | 1500 |
| cccaatcagc attgtcacag tgcttctgga atcctggcac tggaatttaa tgaatgacag | 1560 |
| actctctttg aatccagggc catcatggct ctttgagcaa ggcacagatg gagggagggg | 1620 |
| tcgaagttga aatgggtggg aagagtggtg gggagcatcc tgatttgggg tgggcagaga | 1680 |
| gttgtcatca gaagggttgc agggagagct gcacccaggt ttctgtgggc cttgtcctaa | 1740 |
| tgaatgtggg agaccgggcc atgggcaccc aaaggcagct aagccctgcc caggagagta | 1800 |
| gttgagggt ggagaggggc ttgcttttca gtcattcctc attctgtcct caggaatgtc | 1860 |
| ccaagccttt gagtagggta agcatcatgg ctggcagcct cacaggattg cttctacttc | 1920 |
| aggcagtgtc gtgggcatca ggtgagtgag tcaaggcagt ggggaggtag cacagagcct | 1980 |
| cccttctgcc tcatagtcct ttggtagcct tccagtaagc tggtggtaga cttttagtag | 2040 |
| gtgctcaata aatccttttg agtgactgag accaactttg gggtgaggat tttgttttt | 2100 |
| ttcttttgaa acagagtctt actctgttgc ctgggctgga gtgcagtggt gcaatttgg | 2160 |
| ctcattccaa cctctgcctc ccagattcaa gcgattctct tgcttcagct tcccaggtag | 2220 |
| ctgggattac aggcggccac cactacgccc agctaatttt tgtattttta gtagagacgg | 2280 |
| ggtttcacca tgctggcaag gcaggtctca aactcctcac ctcaggtgat ccgcccacct | 2340 |

```
cggcctccta aagtgctagg attacaggtg tgagcccctg cgcccggcca aggggtgagg    2400
aattttgaaa ccgtgttcag tctctcctag cagatgtgtc cattctccat gtcttcatca    2460
gacctcactc tgcttgtact ccctccctcc caggtgcccg cccctgcatc cctaaaagct    2520
tcggctacag ctcggtggtg tgtgtctgca atgccacata ctgtgactcc tttgaccccc    2580
cgacctttcc tgcccttggt accttcagcc gctatgagag tacacgcagt gggcgacgga    2640
tggagctgag tatggggccc atccaggcta atcacgggg cacaggtaac cattacaccc     2700 ctcacccct gggccaggct gggtcctcct agaggtaaat ggtgtcagtg atcaccatgg     2760
agtttcccgc tgggtactga tacccttatt ccctgtggat gtcctcaggc ctgctactga    2820
ccctgcagcc agaacagaag ttccagaaag tgaagggatt tggaggggcc atgacagatg    2880
ctgctgctct caacatcctt gccctgtcac cccctgccca aaatttgcta cttaaatcgt    2940
acttctctga agaaggtgag gaggaagggg acaagatgac atagagccat tgaaactttt    3000 cgttttctt ttcttttttt aaaattttt tgaggcagaa tctcactctg cccattctgt       3060
cggcgagaca ggagtgcagt ggtgtgatct cccctcacag caacctctgc ctcccaggct    3120
atagtgattc tcctgcctca gcctcctgag tagctggaat tataggcgtg cgccactacc    3180
acctggctaa ttttttgtatt tttagtagag acagggtttc atcatgttga ccaggctagt   3240
cttaaactcc tgacctcaaa tgatatacct gccttggcct cccgaagtgc tggaattaca    3300
agtgtgagcc accgagccca gcagacactt ttctttttc ttttttttt tttgagacag      3360 agtctcgcac tgtcacccag gctggagtgc agtggcacaa tctcagctca ctgcaacctc    3420 cacctccgg gttcaggtga ttctcctgtc tcagcctctc gagtacctgg gattacaggt     3480
gcctgccacc acgcccggct aattttttgt attttttagta gagacagggt ttcactatgt   3540
tggccaggat gattgcgaac tcctgacctc gtgatctgcc cacatcggcc tcccaaagtg    3600
ctgggattac atgcgtgagc cactgacact tttctttgcc cttctttgg accctgactt     3660 ctgcccatcc ctgacatttg gttcctgttt taatgccctg tgaaataaga tttcgccgcc    3720
tatcatctgc taactgctac ggactcaggc tcagaaaggc ctgcgcttca cccaggtgcc    3780
agcctccaca ggttccaacc caggagccca agttcccttt ggccctgact cagacactat    3840
taggactggc aagtgataag cagagtccca tactctccta ttgactcgga ctaccatatc    3900
ttgatcatcc ttttctgtag gaatcggata taacatcatc cgggtaccca tggccagctg    3960
tgacttctcc atccgcacct acacctatgc agacacccct gatgatttcc agttgcacaa    4020
cttcagcctc ccagaggaag ataccaagct caaggtaggc attctagctt tttcaggccc    4080
tgagggccct gatgtctggg ggttgagaaa ctgtagggta ggtctgcttg tacagacatt    4140
ttgtcccctg ctgttttgtc ctgggggtgg gagggtggag gctaatggct gaaccggatg    4200
cactggttgg gctagtatgt gttccaactc tgggtgcttc tctcttcact accttgtct     4260 ctagatalccc ctgattcacc gagccctgca gttggcccag cgtcccgttt cactccttgc   4320
cagcccctgg acatcaccca cttggctcaa gaccaatgga gcggtgaatg ggaagggtc     4380 actcaaggga cagcccggag acatctacca ccagacctgg gccagatact tgtgaagta     4440 agggatcagc aaggatgtgg gatcaggact ggcctcccat ttagccatgc tgatctgtgt    4500
cccaaccctc aacctagttc cacttccaga tctgcctgtc ctcagctcac ctttctacct    4560
tctgggcctt tcagccttgg gcctgtcaat cttgcccact ccatcaggct tcctgttctc    4620
tcggtctggc ccactttctt tttatttttc ttcttttttt ttttttgag aaggagtctc     4680 tctctctgtc acccaggctg gagtgctgtg gcgccatctt cactcactgt aacctctgcc    4740
```

```
tcctgagttc aagcaattct cctgcctcag ccttccaagt agctgggatt ataggcgcct    4800
gccaccaggc ccagctgatt tttctatttt tagtagagac ggggtttcgc caggctgttc    4860
tcgaactcct gaactcaagt gatccacctg cctcggcttc ccaaagtgct gggattacag    4920
gtgtgagcca ccacacccag ctggtctggt ccactttctt ggccggatca ttcatgacct    4980
ttctcttgcc aggttcctgg atgcctatgc tgagcacaag ttacagttct gggcagtgac    5040
agctgaaaat gagccttctg ctgggctgtt gagtggatac cccttccagt gcctgggctt    5100
cacccctgaa catcagcgag acttcattgc ccgtgaccta ggtcctaccc tcgccaacag    5160
tactcaccac aatgtccgcc tactcatgct ggatgaccaa cgcttgctgc tgccccactg    5220
ggcaaaggtg gtaaggcctg gacctccatg gtgctccagt gaccttcaaa tccagcatcc    5280
aaatgactgg ctcccaaact tagagcgatt tctctaccca actatggatt cctagagcac    5340
cattcccctg gacctccagg gtgccatgga tcccacagtt gtcgcttgaa acctttctag    5400
gggctgggcg aggtggctca ctcatgcaaa cccagcactt tgggaagccg aggcgggtga    5460
tcacctgagg tcaggagttt aagaccaccc tggccaacgt gttgaaaccc tgtgtctact    5520
aaaatacaaa aaaaaaaaat tatctgggca tgatggtggg tgtctgtaat cccagctact    5580
caggaggctg agaagggaga atcagttgaa cccgggagat ggtggttgcg gtgagccgag    5640
atcgcgccac tgcactccag cctgggaggc tgagcgagac tccatctcga aacaaaacaa    5700
aacaaaacta tctaggctgg gggtggtggt tcatgtatgt atgtgtatat acatatatat    5760
gtgtttatat gtatatatat atacacacac acacatacat acacacacat acacacacaa    5820
attagctggg tgtggcaccc gtgtagtccc agctactcag gaggctaatg tgggaggatc    5880
agttgaccct aggaagtcaa ggctgcagtg agtcgtgatt gcgccactgt actccagccc    5940
gagtgacaga gtgacatcct gtctcaaaaa caaaaaaaaa tctccccaaa cctctctagt    6000
tgcattcttc ccgtcaccca actccaggat tcctacaaca ggaactagaa gttccagaag    6060
cctgtgtgca aggtccagga tcagttgctc ttcctttgca ggtactgaca gacccagaag    6120
cagctaaata tgttcatggc attgctgtac attggtacct ggactttctg gctccagcca    6180
aagccaccct aggggagaca caccgcctgt tccccaacac catgctcttt gcctcagagg    6240
cctgtgtggg ctccaagttc tgggagcaga gtgtgcggct aggctcctgg gatcgaggga    6300
tgcagtacag ccacagcatc atcacggtaa gccaccccag tctcccttcc tgcaaagcag    6360
acctcagacc tcttactagt ttcaccaaag actgacagaa gcccttcctg tccagctttc    6420
cccagctagc ctgccctttt gagcaactct ggggaaccat gattccctat cttcccttc     6480 cttcacaggt ctgcacacct cattgcccct tttgcaacta ctgaggcact tgcagctgcc    6540
tcagacttct cagctcccct tgagatgcct ggatcttcac accccaact ccttagctac     6600 taaggaatgt gcccctcaca gggctgacct acccacagct gcctctccca catgtgaccc    6660
ttacctacac tctctgggga cccccagtgt tgagcctttg tctctttgcc tttgtcctta    6720
ccctagaacc tcctgtacca tgtggtcggc tggaccgact ggaaccttgc cctgaacccc    6780
gaaggaggac ccaattgggt gcgtaacttt gtcgacagtc ccatcattgt agacatcacc    6840
aaggacacgt tttacaaaca gcccatgttc taccaccttg ccacttcag gtgagtggag     6900 ggcgggcacc cccattccat accaggccta tcatctccta catcggatgg cttacatcac    6960
tctacaccac gagggagcag gaaggtgttc agggtggaac ctcggaagag gcacacccat    7020 cccctttgc accatggagg caggaagtga ctaggtagca acagaaaacc ccaatgcctg     7080
```

```
aggctggact gcgatgcaga aaagcagggt cagtgcccag cagcatggct ccaggcctag    7140
agagccaggg cagagcctct gcaggagtta tggggtgggt ccgtgggtgg gtgacttctt    7200
agatgagggt ttcatgggag gtaccccgag ggactctgac catctgttcc cacattcagc    7260
aagttcattc ctgagggctc ccagagagtg gggctggttg ccagtcagaa gaacgacctg    7320
gacgcagtgg cactgatgca tcccgatggc tctgctgttg tggtcgtgct aaaccggtga    7380
gggcaatggt gaggtctggg aagtgggctg aagacagcgt tggggccctt gcaggatca    7440 cactctcagc ttctcctccc tgctccctag ctcctctaag gatgtgcctc ttaccatcaa    7500
ggatcctgct gtgggcttcc tggagacaat ctcacctggc tactccattc acacctacct    7560
gtggcgtcgc cagtgatgga gcagatactc aaggaggcac tgggctcagc ctgggcatta    7620
aagggacaga gtcagctcac acgctgtctg tgactaaaga gggcacagca gggccagtgt    7680
gagcttacag cgacgtaagc ccaggggcaa tggtttgggt gactcacttt ccctctagg    7740 tggtgccagg ggctggaggc cctagaaaaa gatcagtaa gccccagtgt ccccccagcc    7800
cccatgctta tgtgaacatg cgctgtgtgc tgcttgcttt ggaaactggg cctgggtcca    7860
ggcctagggt gagctcactg tccgtacaaa cacaagatca gggctgaggg taaggaaaag    7920
aagagactag gaaagctggg cccaaaactg gagactgttt gtctttcctg gagatgcaga    7980
actgggcccg tggagcagca gtgtcagcat cagggcggaa gccttaaagc agcagcgggt    8040
gtgcccaggc acccagatga ttcctatggc accagccagg aaaaatgcca gctcttaaag    8100
gagaaaatgt ttgagcccag tcagtgtgag tggctttatt ctgggtggca gcaccccgtg    8160
tccggctgta ccaacaacga ggaggcacgg gggcctctgg aatgcatgag agtagaaaaa    8220
ccagtcttgg gagcgtgagg acaaatcatt cctcttcatc ctcctcagcc atgcccaggg    8280
tccgggtgcc tggggcccga gcaggcgttg cccgctggat ggagacaatg ccgctgagca    8340
aggcgtagcc caccatggct gccagtcctg ccagcacaga taggatctgg ttccggcgcc    8400
ggtatggctc ctcctcagtc tctgggcctg ctggtgtctg gcgttgcggt ggtacctcag    8460
ctgagggtca aggaaggaag gtgtgttagg agaactagtt cttggatccc tgcccactct    8520
ccccagggct gccccttccca tctgccccctt acctccatcc caggggaagt agagactgag    8580
aatgtgggta caataggcac agaggttgtg cagcccacgc aggtggacct gcagcttccc    8640
actgggcagc tttgcctgca gcagcagggc caagtagctg aagacgaagg cgtccaagga    8700
ggcagggctg gagcagagag agaagggtgg gatggaggag aaccactggg gtagaagggg    8760
taaagatgga gctggaggaa gagtcagcct tgggaggtgg gctctgggca gcaggcggcc    8820
accaggaagg acaggacaca cagttctaga                                    8850
```

<210> SEQ ID NO 2
<211> LENGTH: 536
<212> TYPE: PRT
<213> ORGANISM: Homo sapiens

<400> SEQUENCE: 2

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

-continued

```
Phe Asp Pro Pro Thr Phe Pro Ala Leu Gly Thr Phe Ser Arg Tyr Glu
 65                  70                  75                  80

Ser Thr Arg Ser Gly Arg Arg Met Glu Leu Ser Met Gly Pro Ile Gln
                 85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
450                 455                 460

Phe Ile Pro Glu Gly Ser Gln Arg Val Gly Leu Val Ala Ser Gln Lys
465                 470                 475                 480
```

Asn Asp Leu Asp Ala Val Ala Leu Met His Pro Asp Gly Ser Ala Val
            485                 490                 495

Val Val Val Leu Asn Arg Ser Ser Lys Asp Val Pro Leu Thr Ile Lys
        500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
        530             535

<210> SEQ ID NO 3
<211> LENGTH: 2586
<212> TYPE: DNA
<213> ORGANISM: Homo sapiens
<220> FEATURE:
<221> NAME/KEY: misc_feature
<222> LOCATION: (2317)..(2317)
<223> OTHER INFORMATION: n is a, c, g, or t

<400> SEQUENCE: 3

| | | | | | |
|---|---|---|---|---|---|
| cattaggcct | atgaattata | agatacagtc | actttaaaat | ccactggaag | gctgaagagt | 60 |
| gagttaaacc | tcttataatg | aatatacagt | gaaaccagta | gaggcatttt | atttagggtt | 120 |
| cctacaagaa | agtgcttaaa | tagcatcgac | gcctacatgc | tacatcctgt | tcagtctctg | 180 |
| cctctgtgat | gcagttggcc | agcaaatatc | ctccaagtca | tcatttgcat | agtgctaggg | 240 |
| ataaaatgag | gagcaatacc | aaatgctata | cctgccctta | tgggtcttat | agtccaacgg | 300 |
| gagaaaaaga | tattatacaa | ataatcacgg | aaaataaata | gaaaacgcat | ccttgttttt | 360 |
| gtttagtgga | tcctctatcc | ttcagagact | ctggaacccc | tgtggtcttc | tcttcatcta | 420 |
| atgaccctga | ggggatggag | ttttcaagtc | cttccagaga | ggaatgtccc | aagcctttga | 480 |
| gtagggtaag | catcatggct | ggcagcctca | caggtttgct | tctacttcag | gcagtgtcgt | 540 |
| gggcatcagg | tgcccgcccc | tgcatcccta | aaagcttcgg | ctacagctcg | gtggtgtgtg | 600 |
| tctgcaatgc | cacatactgt | gactcctttg | acccccgac | cttcctgcc | cttggtacct | 660 |
| tcagccgcta | tgagagtaca | cgcagtgggc | gacggatgga | gctgagtatg | gggcccatcc | 720 |
| aggctaatca | cacgggcaca | ggcctgctac | tgaccctgca | gccagaacag | aagttccaga | 780 |
| aagtgaaggg | atttggaggg | gccatgacag | atgctgctgc | tctcaacatc | cttgccctgt | 840 |
| cacccctgc | ccaaaatttg | ctacttaaat | cgtacttctc | tgaagaagga | atcggatata | 900 |
| acatcatccg | ggtacccatg | gccagctgtg | acttctccat | ccgcacctac | acctatgcag | 960 |
| acaccctga | tgatttccag | ttgcacaact | tcagcctccc | agaggaagat | accaagctca | 1020 |
| agataccct | gattcaccga | gccctgcagt | tggcccagcg | tcccgtttca | ctccttgcca | 1080 |
| gcccctggac | atcacccact | tggctcaaga | ccaatggagc | ggtgaatggg | aagggtcac | 1140 |
| tcaagggaca | gcccggagac | atctaccacc | agacctgggc | cagatacttt | gtgaagttcc | 1200 |
| tggatgccta | tgctgagcac | aagttacagt | tctgggcagt | gacagctgaa | atgagcctt | 1260 |
| ctgctgggct | gttgagtgga | tacccctcc | agtgcctggg | cttcaccct | gaacatcagc | 1320 |
| gagacttcat | tgcccgtgac | ctaggtccta | ccctcgccaa | cagtactcac | cacaatgtcc | 1380 |
| gcctactcat | gctggatgac | caacgcttgc | tgctgcccca | ctgggcaaag | gtggtactga | 1440 |
| cagacccaga | agcagctaaa | tatgttcatg | gcattgctgt | acattggtac | ctggactttc | 1500 |
| tggctccagc | caaagccacc | ctaggggaga | cacaccgcct | gttccccaac | accatgctct | 1560 |
| ttgcctcaga | ggcctgtgtg | ggctccaagt | tctgggagca | gagtgtgcgg | ctaggctcct | 1620 |
| gggatcgagg | gatgcagtac | agccacagca | tcatcacgaa | cctcctgtac | catgtggtcg | 1680 |

```
gctggaccga ctggaacctt gccctgaacc ccgaaggagg acccaattgg gtgcgtaact    1740
ttgtcgacag tcccatcatt gtagacatca ccaaggacag gttttacaaa cagcccatgt    1800
tctaccacct tggccacttc agcaagttca ttcctgaggg ctcccagaga gtggggctgg    1860
ttgccagtca gaagaacgac ctggacgcag tggcactgat gcatcccgat ggctctgctg    1920
ttgtggtcgt gctaaaccgc tcctctaagg atgtgcctct taccatcaag gatcctgctg    1980
tgggcttcct ggagacaatc tcacctggct actccattca cacctacctg tggcatcgcc    2040
agtgatggag cagatactca aggaggcact gggctcagcc tgggcattaa agggacagag    2100
tcagctcaca cgctgtctgt gactaaagag ggcacagcag ggccagtgtg agcttacagc    2160
gacgtaagcc caggggcaat ggtttgggtg actcactttc ccctctaggt ggtgcccagg    2220
gctggaggcc cctagaaaaa gatcagtaag ccccagtgtc cccccagccc ccatgcttat    2280
gtgaacatgc gctgtgtgct gcttgctttg gaaactngcc tgggtccagg cctagggtga    2340
gctcactgtc cgtacaaaca caagatcagg gctgagggta aggaaaagaa gagactagga    2400
aagctgggcc caaaactgga gactgtttgt cttcctaga gatgcagaac tgggcccgtg    2460
gagcagcagt gtcagcatca gggcggaagc cttaaagcag cagcgggtgt gcccaggcac    2520
ccagatgatt cctatggcac cagccaggaa aaatggcagc tcttaaagga gaaatgttt     2580 gagccc                                                              2586

<210> SEQ ID NO 4
<211> LENGTH: 516
<212> TYPE: PRT
<213> ORGANISM: Homo sapiens

<400> SEQUENCE: 4

Met Ala Gly Ser Leu Thr Gly Leu Leu Leu Gln Ala Val Ser Trp
1               5                   10                  15

Ala Ser Gly Ala Arg Pro Cys Ile Pro Lys Ser Phe Gly Tyr Ser Ser
            20                  25                  30

Val Val Cys Val Cys Asn Ala Thr Tyr Cys Asp Ser Phe Asp Pro Pro
        35                  40                  45

Thr Phe Pro Ala Leu Gly Thr Phe Ser Arg Tyr Glu Ser Thr Arg Ser
    50                  55                  60

Gly Arg Arg Met Glu Leu Ser Met Gly Pro Ile Gln Ala Asn His Thr
65                  70                  75                  80

Gly Thr Gly Leu Leu Leu Thr Leu Gln Pro Glu Gln Lys Phe Gln Lys
                85                  90                  95

Val Lys Gly Phe Gly Gly Ala Met Thr Asp Ala Ala Ala Leu Asn Ile
            100                 105                 110

Leu Ala Leu Ser Pro Pro Ala Gln Asn Leu Leu Leu Lys Ser Tyr Phe
        115                 120                 125

Ser Glu Glu Gly Ile Gly Tyr Asn Ile Ile Arg Val Pro Met Ala Ser
    130                 135                 140

Cys Asp Phe Ser Ile Arg Thr Tyr Thr Tyr Ala Asp Thr Pro Asp Asp
145                 150                 155                 160

Phe Gln Leu His Asn Phe Ser Leu Pro Glu Glu Asp Thr Lys Leu Lys
                165                 170                 175

Ile Pro Leu Ile His Arg Ala Leu Gln Leu Ala Gln Arg Pro Val Ser
            180                 185                 190

Leu Leu Ala Ser Pro Trp Thr Ser Pro Thr Trp Leu Lys Thr Asn Gly
        195                 200                 205
```

```
Ala Val Asn Gly Lys Gly Ser Leu Lys Gly Gln Pro Gly Asp Ile Tyr
        210             215             220
His Gln Thr Trp Ala Arg Tyr Phe Val Lys Phe Leu Asp Ala Tyr Ala
225             230             235             240
Glu His Lys Leu Gln Phe Trp Ala Val Thr Ala Glu Asn Glu Pro Ser
                245             250             255
Ala Gly Leu Leu Ser Gly Tyr Pro Phe Gln Cys Leu Gly Phe Thr Pro
            260             265             270
Glu His Gln Arg Asp Phe Ile Ala Arg Asp Leu Gly Pro Thr Leu Ala
        275             280             285
Asn Ser Thr His His Asn Val Arg Leu Leu Met Leu Asp Asp Gln Arg
    290             295             300
Leu Leu Leu Pro His Trp Ala Lys Val Val Leu Thr Asp Pro Glu Ala
305             310             315             320
Ala Lys Tyr Val His Gly Ile Ala Val His Trp Tyr Leu Asp Phe Leu
                325             330             335
Ala Pro Ala Lys Ala Thr Leu Gly Glu Thr His Arg Leu Phe Pro Asn
            340             345             350
Thr Met Leu Phe Ala Ser Glu Ala Cys Val Gly Ser Lys Phe Trp Glu
        355             360             365
Gln Ser Val Arg Leu Gly Ser Trp Asp Arg Gly Met Gln Tyr Ser His
    370             375             380
Ser Ile Ile Thr Asn Leu Leu Tyr His Val Val Gly Trp Thr Asp Trp
385             390             395             400
Asn Leu Ala Leu Asn Pro Glu Gly Gly Pro Asn Trp Val Arg Asn Phe
                405             410             415
Val Asp Ser Pro Ile Ile Val Asp Ile Thr Lys Asp Thr Phe Tyr Lys
            420             425             430
Gln Pro Met Phe Tyr His Leu Gly His Phe Ser Lys Phe Ile Pro Glu
        435             440             445
Gly Ser Gln Arg Val Gly Leu Val Ala Ser Gln Lys Asn Asp Leu Asp
    450             455             460
Ala Val Ala Leu Met His Pro Asp Gly Ser Ala Val Val Val Val Leu
465             470             475             480
Asn Arg Ser Ser Lys Asp Val Pro Leu Thr Ile Lys Asp Pro Ala Val
                485             490             495
Gly Phe Leu Glu Thr Ile Ser Pro Gly Tyr Ser Ile His Thr Tyr Leu
            500             505             510
Trp His Arg Gln
        515
```